United States Patent [19]

Bailey

[11] 4,169,108
[45] Sep. 25, 1979

[54] 5(OR 6)-[SUBSTITUTED-AMINO)ALKYL]-2,3-NAPHTHALENEDIOLS

[75] Inventor: Denis M. Bailey, East Greenbush, N.Y.

[73] Assignee: Sterling Drug Inc., New York, N.Y.

[21] Appl. No.: 388,962

[22] Filed: Aug. 16, 1973

[51] Int. Cl.$^2$ .............................................. C07C 87/28

[52] U.S. Cl. .................. 260/570.8 R; 260/239 B; 260/326.4; 260/326.5 C; 260/326.5 J; 260/340.5 R; 260/340.9 R; 260/465 F; 260/501.12; 260/501.18; 260/501.19; 424/278; 562/467; 260/544 B; 568/633; 568/586; 260/559 D; 260/562 P; 260/566 R; 260/566 A; 260/570.5 R; 260/570.5 C; 260/570.6; 260/570.9; 260/586 P; 260/599; 260/592; 424/248.57; 424/268; 424/274; 424/316; 424/330; 544/138; 544/176; 500/8; 500/19; 500/100; 500/139; 500/142; 500/196; 546/206; 562/444

[58] Field of Search .................. 260/570.81 R, 501.18

[56] References Cited

U.S. PATENT DOCUMENTS

| | | | |
|---|---|---|---|
| 2,119,077 | 5/1938 | Hill et al. ........................... | 260/570.8 |
| 3,046,117 | 7/1962 | Sus ..................................... | 260/141 X |
| 3,573,304 | 3/1971 | Eberle et al. ................ | 260/570.8 X |

*Primary Examiner*—Robert V. Hines
*Attorney, Agent, or Firm*—Paul E. Dupont; B. Woodrow Wyatt

[57] ABSTRACT

Aminoalkylnaphthols and esters thereof, useful as cardiotonic agents, prepared from the corresponding RO-naphthalenealkylamines, certain of which are also useful as cardiotonic agents, are disclosed.

20 Claims, No Drawings

5(OR 6)-[(SUBSTITUTED-AMINO)ALKYL]-2,3-NAPHTHALENEDIOLS

The present invention relates to substituted aminoalkylnaphthols and esters thereof, and to processes and intermediates for the preparation of the same.

In one of its composition aspects, the invention sought to be patented resides in the chemical compounds designated as substituted aminoalkyl-A-2,3-naphthalenediols having, in the free base form, the formula I hereinbelow:

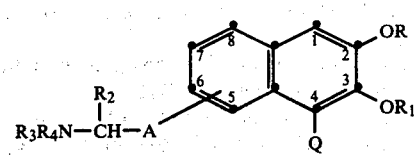

wherein the side chain represented by

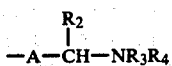

occupies either position 5 or position 6 of the naphthalene nucleus;

R and $R_1$ are independently hydrogen, lower-alkanoyl or aroyl;

Q is hydrogen or methyl;

A is carbonyl, CHOH, a direct linkage or $CR_5R_6$ where $R_5$ and $R_6$ are independently hydrogen or methyl;

$R_2$ is hydrogen or methyl, provided that when X is a direct linkage, or when $R_5$ and/or $R_6$ are methyl, then $R_2$ is hydrogen;

$R_3$ and $R_4$ are independently hydrogen, lower-alkyl, benzyl, aryl, or $NR_3R_4$ is pyrrolidino, piperidino, hexamethyleneimino, morpholino or any of these having from one to two lower-alkyl substituents.

The compounds of the invention having, in the free base form, the formula I hereinabove are useful as cardiotonic agents as described more fully hereinbelow. Furthermore, the diols of formula I (R=$R_1$=H; A is C=O, a direct linkage, or $CR_5R_6$ as defined hereinabove) are also used to prepare the corresponding ester derivatives wherein at least one of R and $R_1$ is lower-alkanoyl or aroyl while the other is hydrogen, or wherein both R and $R_1$ are lower-alkanoyl or aroyl. The compounds of formula I wherein A is carbonyl are also useful as intermediates in the preparation of the corresponding alcohols having formula I wherein A is CHOH.

Because of high cardiotonic activity, preferred embodiments of the present invention reside in the chemical compounds designated as substituted 6-aminoethyl-A-2,3-naphthalenediols having, in the free base form, the formula I hereinabove wherein:

the side chain represented by

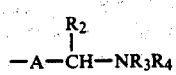

occupies position 6 of the naphthalene nucleus;

R, $R_1$, and $R_2$ are hydrogen;

A is $CR_5R_6$ where $R_5$ and $R_6$ are both hydrogen;

$R_3$, $R_4$ and $NR_3R_4$ have the same significance indicated hereinabove.

Particularly preferred species are 6-(2-aminoethyl)-2,3-naphthalenediol, 6-[2-(ethylamino)ethyl]-2,3-naphthalenediol and 6-[2-(1-pyrrolidinyl)ethyl]-2,3-naphthalenediol.

In another composition aspect, the invention resides in the chemical compounds having, in the free base form, the formula II hereinbelow:

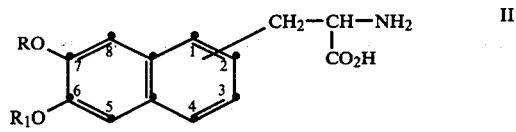

wherein the side chain represented by

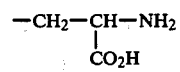

occupies either position 1 or position 2 of the naphthalene nucleus, and

R and $R_1$ are independently hydrogen, lower-alkanoyl or aroyl.

These amino acid derivatives of formula II are useful as cardiotonic agents.

In yet another composition aspect, the invention resides in the chemical compounds designated as substituted aminoalkylnaphthalenediols having in the free base form, the formula III hereinbelow:

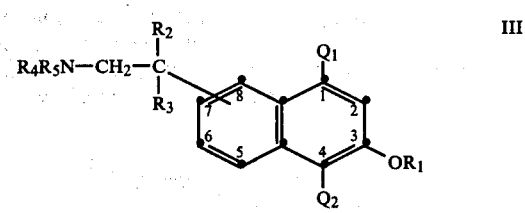

wherein the side chain represented by

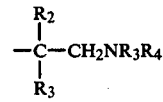

occupies either position 7 or position 8 of the naphthalene nucleus;

$Q_1$ and $Q_2$ are each hydrogen or OR provided that $Q_1$ and $Q_2$ are not simultaneously hydrogen or OR;

R and $R_1$ are independently hydrogen, lower-alkanoyl or aroyl;

$R_2$ and $R_3$ are independently hydrogen or methyl, and $R_4$ and $R_5$ are independently hydrogen, lower-alkyl, aryl, or $NR_4R_5$ is pyrrolidino, piperidino, hexamethyleneimino, morpholino, or any of these having from one to two lower-alkyl substituents.

The compounds of the invention having, in the free base form, the formula III hereinabove are useful as cardiotonic agents.

In still another composition aspect, the invention resides in the chemical compounds designated as substituted aminoalkyl-1,5-naphthalenediols having, in the free base form, the formula IV hereinbelow:

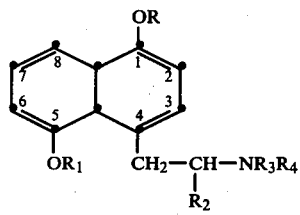

wherein R and $R_1$ are independently hydrogen, lower-alkanoyl or aroyl;

$R_2$ is hydrogen or methyl, and $R_3$ and $R_4$ are independently hydrogen, lower-alkyl, aryl, or $NR_2R_3$ is pyrrolidino, piperidino, hexamethyleneimino, morpholino, or any of these having from one to two lower-alkyl substituents.

The compounds of the invention having, in the free base form, the formula IV hereinabove are useful as cardiotonic agents.

In a further composition aspect, the invention sought to be patented resides in the chemical compounds designated as substituted aminoalkyl-2-naphthols having, in the free base form, the formula V hereinbelow:

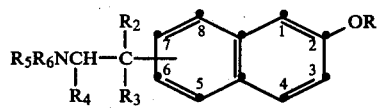

wherein the side chain represented by

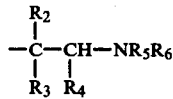

occupies either position 6 or position 7 of the naphthalene nucleus;

R is hydrogen, lower-alkanoyl, or aroyl;

$R_2$, $R_3$ and $R_4$ are each hydrogen or methyl provided that when $R_4$ is methyl, $R_2$ and $R_3$ are hydrogen;

$R_5$ and $R_6$ are hydrogen, lower-alkyl, benzyl, aryl, or $NR_5R_6$ is pyrrolidino, piperidino, hexamethyleneimino, morpholino, or any of these having from one to two lower-alkyl substituents.

The compounds of the invention having, in the free base form, the formula V hereinabove are useful as cardiotonic agents. Because of high cardiotonic activity a preferred species of formula V is 6-(2-aminoethyl)-2-naphthol.

Another composition aspect of the invention resides in the chemical compounds having, in the free base form, the formula VI hereinbelow:

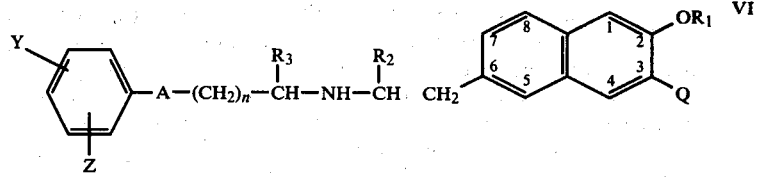

wherein Q is hydrogen or OR;

R and $R_1$ are independently hydrogen, lower-alkanoyl or aroyl;

$R_2$ and $R_3$ are independently hydrogen or methyl;

A is methylene, carbonyl, or CHOH;

Y and Z may be the same or different and are chosen from the group consisting of hydrogen, hydroxy, methoxy, lower-alkanoyloxy, or aroyloxy, and n is 0 or 1.

The compounds having, in the free base form, the formula VI are useful as cardiotonic agents.

In another composition aspect, the invention sought to be patented resides in the chemical compounds having, in the free base form, the formula VII hereinbelow:

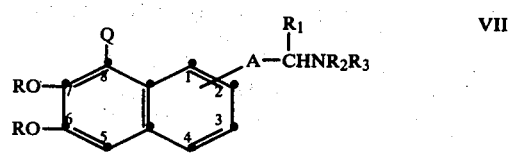

wherein the side chain represented by

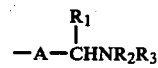

occupies either position 1 or position 2 of the naphthalene nucleus;

R is lower-alkyl or benzyl; or both R groups together constitute a methylene group bonded to both oxygen atoms;

Q is hydrogen or methyl;

A is carbonyl, a direct linkage or $CR_4R_5$ where $R_4$ and $R_5$ are independently hydrogen or methyl;

$R_1$ is hydrogen or methyl, provided that when A is a direct linkage, or when $R_4$ and/or $R_5$ are methyl then $R_1$ is hydrogen, and $R_2$ and $R_3$ are independently hydrogen, lower-alkyl, benzyl, aryl, or $NR_2R_3$ is pyrrolidino, piperidino, hexamethyleneimino, morpholino, or any of these having from one to two lower-alkyl substituents.

The compounds of the invention having, in the free base form, the formula VII hereinabove are useful as cardiotonic agents and are also useful as intermediates in the preparation of the compounds of this invention having the formula I (A is C=O, a direct linkage, or $CR_5R_6$ as defined hereinabove). In addition, the amines of formula VII wherein A is methylene, and Q, $R_2$ and $R_3$ are hydrogen are useful as intermediates in the preparation of the compounds of formula XII described hereinbelow. The amino ketones VII (A is C=O) are also useful as intermediates in the preparation of the amines of formula VII wherein A is methylene.

Because of high cardiotonic activity, preferred species of formula VII are those wherein:

The side chain represented by

occupies position 2 of the naphthalene nucleus;

R is lower-alkyl;

$R_1$ is hydrogen;

A is $CR_4R_5$ where $R_4$ and $R_5$ are both hydrogen;

$R_2$, $R_3$ and $NR_2R_3$ have the same significance indicated hereinabove.

Particularly preferred species are N-ethyl-6,7-dimethoxynaphthaleneethylamine, N,N-dimethyl-6,7-dimethoxynaphthaleneethylamine, 1-[2-(6,7-dimethoxy-2-naphthyl)ethyl]pyrrolidine, and 1-[2-(6,7-dimethoxy-2-naphthyl)ethyl]piperidine.

Another composition aspect of the invention resides in the chemical compound having the formula VIII hereinbelow:

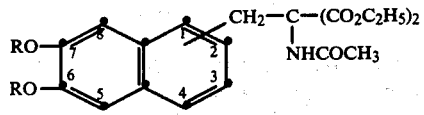

wherein the side chain represented by

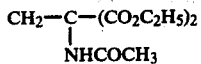

occupies either position 1 or position 2 of the naphthalene nucleus, and

R is lower-alkyl or benzyl; or both R groups together constitute a methylene group bonded to both oxygen atoms.

These compounds are useful as intermediates in the preparation of the alanine derivatives of formula II hereinabove.

In another composition aspect, the invention resides in the chemical compounds designated as dialkoxynaphthalenealkylamines having in the free base form, the formula IX hereinbelow:

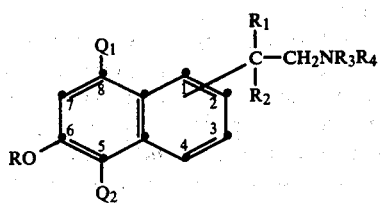

wherein the side chain represented by

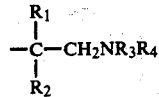

occupies either position 1 or position 2 of the naphthalene nucelus;

$Q_1$ and $Q_2$ are each hydrogen or OR provided that $Q_1$ and $Q_2$ are not simultaneously hydrogen or OR;

R is lower-alkyl;

$R_1$ and $R_2$ are independently hydrogen, or methyl, and $R_3$ and $R_4$ are independently hydrogen, lower-alkyl, aryl, or $NR_3R_4$ is pyrrolidino, piperidino, hexamethyleneimino, morpholino, or any of these having from one to two lower-alkyl substituents.

These compounds are useful as intermediates in the preparation of the compounds of the invention having formula III hereinabove.

The invention resides, in another of its composition aspects, in the chemical compounds having, in the free base form, the formula X hereinbelow:

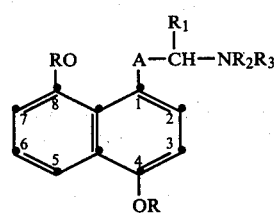

wherein R is lower-alkyl;

A is carbonyl, CHOH or methylene;

$R_1$ is hydrogen or methyl, and $R_2$ and $R_3$ are independently hydrogen, lower-alkyl, or aryl, and $NR_2R_3$ is pyrrolidino, piperidino, hexamethyleneimino, morpholino, or any of these having from one to two lower-alkyl substituents.

The compounds of formula X wherein A is methylene are useful as intermediates in the preparation of the compounds of formula IV hereinabove. The aminoketones X wherein A is C=O are useful as intermediates in the preparation of both the amino alcohols X wherein A is CHOH as well as the amines of formula X wherein A is methylene. The aminoalcohols X wherein A is CHOH are also valuable intermediates in the preparation of the amines X wherein A is methylene.

In another composition aspect, the invention resides in the chemical compounds having, in the free base form, the formula XI hereinbelow:

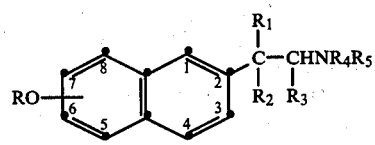

wherein the RO— substituent occupies either position 6 or position 7 of the naphthalene nucleus;

R is lower-alkyl or benzyl;

$R_1$, $R_2$ and $R_3$ are each hydrogen or methyl, provided that when $R_3$ is methyl $R_1$ and $R_2$ are hydrogen;

$R_4$ and $R_5$ are independently hydrogen, lower-alkyl, benzyl, aryl, or $NR_4R_5$ is pyrrolidino, piperidino, hexamethyleneimino, morpholino, or any of these having from one to two lower-alkyl substituents.

These compounds are useful as cardiotonic agents and are useful also as intermediates in preparing the compounds of formula V hereinabove.

In another of its composition aspects, the invention sought to be patented resides in the chemical compounds having, in the free base form, the formula XII hereinbelow:

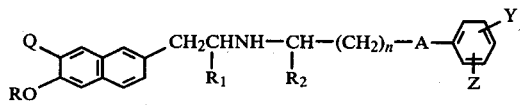

XII wherein Q is hydrogen or OR;
R is lower-alkyl or benzyl;
$R_1$ and $R_2$ are independently hydrogen or methyl;
A is methylene, carbonyl or CHOH;
Y and Z may be the same or different and are chosen from the group consisting of hydrogen, hydroxy and methoxy, and
n is 0 or 1.

The compounds having, in the free base form, the formula XII are useful as intermediates in the preparation of the compounds of formula VI hereinabove.

Another composition aspect of the invention resides in the chemical compounds having, in the free base form, the formula XIII hereinbelow:

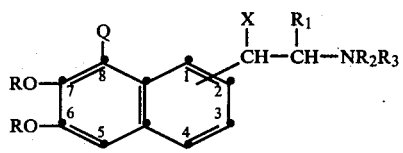

XIII wherein the side chain represented by —CHX—CHR$_1$NR$_2$R$_3$ occupies either position 1 or position 2 of the naphthalene nucleus;
R is lower-alkyl or benzyl; or both R groups together constitute a methylene group bonded to both oxygen atoms;
X is chlorine or bromine;
Q and $R_1$ are independently hydrogen or methyl, and
$R_2$ and $R_3$ are independently hydrogen, lower-alkyl, benzyl, aryl, or
NR$_2$R$_3$ is pyrrolidino, piperidino, hexamethyleneimino, morpholino, or any of these having from one to two lower-alkyl substituents.

The haloamines XIII are useful as intermediates in the preparation of the amines of formula VII hereinabove wherein A is methylene.

Another composition aspect of the invention resides in the chemical compounds having the formula XIV hereinbelow:

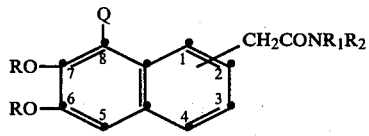

XIV wherein the side chain represented by —CH$_2$CONR$_1$R$_2$ occupies either position 1 or position 2 of the naphthalene nucleus;
R is lower-alkyl or benzyl; or both R groups together constitute a methylene group bonded to both oxygen atoms;

Q is hydrogen or methyl, and
$R_1$ and $R_2$ are independently hydrogen, lower-alkyl, benzyl, aryl, or
NR$_1$R$_2$ is pyrrolidino, piperidino, hexamethyleneimino, morpholino, or any of these having from one to two lower-alkyl substituents.

These amides are useful as intermediates in the preparation of the corresponding amines of formula VII hereinabove, wherein A is methylene and $R_1$ is hydrogen.

In a further composition aspect of the invention resides in the chemical compounds having the formula XV hereinbelow:

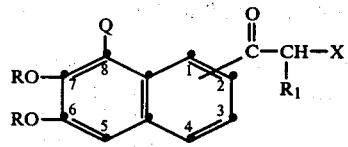

XV wherein the side chain represented by —COCHR$_1$X occupies either position 1 or position 2 of the naphthalene nucleus;
R is lower-alkyl or benzyl; or both R groups together constitute a methylene group bonded to both oxygen atoms;
Q and $R_1$ are independently hydrogen or methyl, and
X is chlorine, bromine or iodine.

The halo ketones (XV) are useful as intermediates in the preparation of the corresponding amino ketones of formula VII hereinabove wherein A is carbonyl.

Another composition aspect of the invention resides in the chemical compounds having the formula XVI hereinbelow:

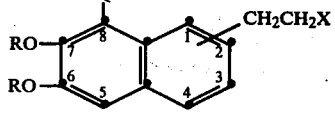

XVI wherein the side chain represented by —CH$_2$CH$_2$X occupies either position 1 or position 2 of the naphthalene nucleus;
R is lower-alkyl or benzyl; or both R groups together constitute a methylene group bonded to both oxygen atoms;
Q is hydrogen or methyl, and
X is chlorine, bromine or p-toluenesulfonate.

These compounds are useful as intermediates in the preparation of the amines of formula VII hereinabove wherein A is methylene and $R_1$ is hydrogen.

In another composition aspect, the invention resides in the chemical compounds having the formula XVII hereinbelow:

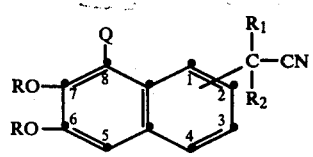

XVII wherein the side chain represented by

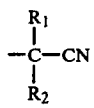

occupies either position 1 or position 2 of the naphthalene nucleus;

R is lower-alkyl or benzyl; or both R groups together constitute a methylene group bonded to both oxygen atoms, and Q, $R_1$ and $R_2$ are independently hydrogen or methyl.

These nitriles are useful as intermediates in the preparation of the amines having fromula VII hereinabove, wherein A is $CR_4R_5$ and $R_1$ is hydrogen.

The nitriles of formula XVII wherein $R_1$ and $R_2$ are hydrogen are useful as intermediates in the preparation of the nitriles of formula XVII wherein one of or both $R_1$ and $R_2$ are methyl.

In another composition aspect, the invention resides in the chemical compounds having the formula XVIII hereinbelow:

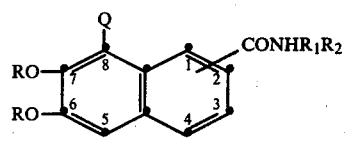

XVIII wherein the side chain represented by —$CONR_1R_2$ occupies either position 1 or position 2 of the naphthalene nucleus;

Q is hydrogen or methyl;

R is lower-alkyl or benzyl; or both R groups together constitute a methylene group bonded to both oxygen atoms;

$R_1$ and $R_2$ are independently hydrogen, lower-alkyl, benzyl, or aryl provided that when the side chain —$CONR_1R_2$ occupies position 2, $R_1$ and $R_2$ are not both hydrogen;

$NR_1R_2$ is pyrrolidino, piperidino, hexamethyleneimino, morpholino, or any of these having from one to two lower-alkyl substituents.

These naphthamides are useful as intermediates in the preparation of the amines of formula VII hereinabove wherein A is a direct linkage; and wherein $R_2$ and $R_3$ are not both hydrogen when the aminomethyl group —$CH_2NR_2R_3$ occupies position 2 of the naphthalene nucleus.

In another composition aspect, the invention resides in the chemical compounds having the formula XIX hereinbelow:

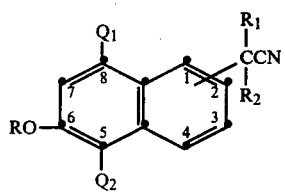

XIX wherein the side chain represented by

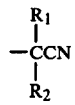

occupies either position 1 or position 2 of the naphthalene nucleus;

$Q_1$ and $Q_2$ are each hydrogen or OR, provided that $Q_1$ and $Q_2$ are not simultaneously hydrogen or OR;

R is lower-alkyl, and $R_1$ and $R_2$ are independently hydrogen or methyl.

These nitriles are useful as intermediates in the preparation of the corresponding amines of formula IX hereinabove. The nitriles XIX wherein $R_1$ and $R_2$ are hydrogen are useful as intermediates in the preparation of the nitriles of formula XIX wherein $R_1$ and/or $R_2$ represent methyl.

Another composition aspect of the present invention resides in the chemical compounds having the formula XX hereinbelow:

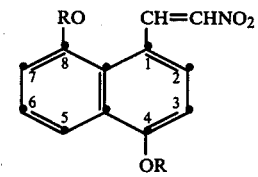

XX wherein R is lower-alkyl or benzyl.

The nitro-olefins (XX) of the invention are useful as intermediates in the preparation of the amines of formula X hereinabove wherein A is methylene and $R_1$, $R_2$ and $R_3$ are hydrogen.

A further composition aspect of the invention resides in the chemical compounds having the formula XXI hereinbelow:

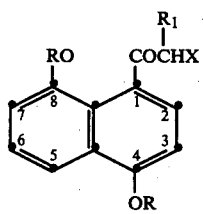

XXI wherein R is lower-alkyl, $R_1$ is hydrogen or methyl, and

X is chlorine, bromine or iodine.

These halo ketones are useful as intermediates in the preparation of the corresponding amino ketones of formula X hereinabove wherein A is carbonyl.

A further composition aspect of the invention resides in the chemical compounds having the formula XXII hereinbelow:

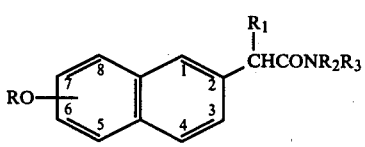

wherein the RO-substituent occupies either position 6 or position 7 of the naphthalene nucleus;

R is lower-alkyl or benzyl;

$R_1$ is hydrogen or methyl, and $R_2$ and $R_3$ are independently hydrogen, lower-alkyl, benzyl, aryl, or $NR_2R_3$ is pyrrolidino, piperidino, hexamethyleneimino, morpholino, or any of these having from one to two lower-alkyl substituents.

These amides are useful as intermediates in the preparation of the RO-2-naphthalenealkylamines of formula XI hereinabove, wherein $R_2$ and $R_3$ are hydrogen.

Another composition aspect of the invention resides in the chemical compounds having the formula XXIII hereinbelow:

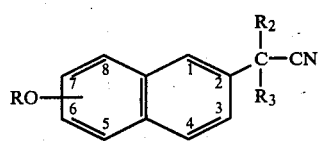

wherein the RO substituent occupies either position 6 or position 7 of the naphthalene nucleus;

R is lower-alkyl or benzyl, and $R_2$ and $R_3$ are independently hydrogen or methyl.

The nitriles XXIII are useful as intermediates in the preparation of the (RO)-naphthalenealkylamines of formula XI hereinabove, wherein $R_3$ is hydrogen. Furthermore the nitriles XXIII wherein $R_2$ and $R_3$ are hydrogen are useful as intermediates in the preparation of nitriles XXIII wherein either one of or both $R_2$ and $R_3$ are methyl.

A further composition aspect of the invention resides in the chemical compounds having the formula XXIV hereinbelow:

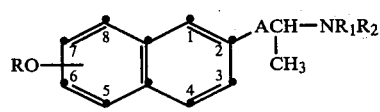

wherein the RO substituent occupies either position 6 or position 7 of the naphthalene nucleus;

A is carbonyl or CHOH;

R is lower-alkyl;

$R_1$ and $R_2$ are independently hydrogen, lower-alkyl, benzyl, aryl, or $NR_1R_2$ is pyrrolidino, piperidino, hexamethyleneimino, morpholino, or any of these having from one to two lower-alkyl substituents.

These compounds are useful as intermediates in the preparation of the amines of formula XI wherein $R_1$ and $R_2$ are hydrogen and $R_3$ is methyl. Furthermore the aminoketones XXIV (A is C=O) are useful as intermediates in the preparation of the corresponding aminoalcohols XXIV (A is CHOH).

The invention, in another composition aspect, resides in the chemical compounds having, in the free base form, the formula XXV hereinbelow:

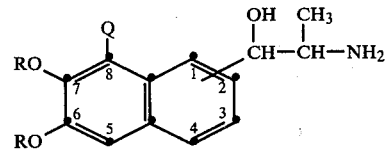

wherein the side chain represented by $$\underset{\underset{CH}{|}}{OH} \underset{\underset{CHNR_1R_2}{|}}{CH_3}$$

occupies either position 1 or position 2 of the naphthalene nucleus;

R is lower-alkyl or benzyl; or both R groups together constitute a methylene group bonded to both oxygen atoms, and Q is hydrogen or methyl.

These hydroxy amines are useful as intermediates in the preparation of the haloamines of formula XIII hereinabove wherein $R_1$ is methyl and $R_2$ and $R_3$ are hydrogen.

Another composition aspect of this invention resides in the chemical compounds having the formula XXVI hereinbelow:

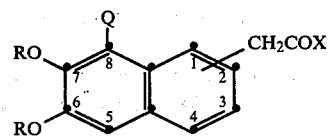

wherein the side chain represented by —$CH_2COX$ occupies either position 1 or position 2 of the naphthalene nucleus;

R is lower-alkyl or benzyl; or both R groups together constitute a methylene group bonded to both oxygen atoms;

Q is hydrogen or methyl, and

X is chlorine or bromine.

These acid halides are useful as intermediates in the preparation of the naphthaleneacetamides of formula XIV hereinabove.

In another composition aspect, the invention resides in the chemical compounds having the formula XXVII hereinbelow:

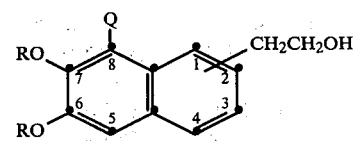

wherein the side chain represented by —$CH_2CH_2OH$ occupies either position 1 or position 2 of the naphthalene nucleus;

R is lower-alkyl or benzyl; or both R groups together constitute a methylene group bonded to both oxygen atoms, and Q is hydrogen or methyl.

These alcohols are useful as intermediates in the preparation of the corresponding halides of formula XVI hereinabove.

Another composition aspect of the invention resides in the chemical compounds having the formula XXVIII hereinbelow:

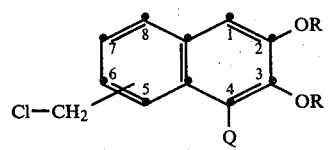

wherein the chloromethyl substituent occupies either position 5 or position 6 of the naphthalene nucleus;

R is lower-alkyl or benzyl; or both R groups together constitute a methylene group bonded to both oxygen atoms, and Q is hydrogen or methyl.

These halides are useful as intermediates in the preparation of the nitriles of formula XVII ($R_1=R_2=H$) as well as the amino acid derivatives of formula VIII hereinabove.

A further composition aspect of the invention resides in the chemical compounds having the formula XXIX hereinbelow:

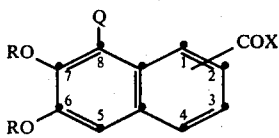    XXIX wherein the halocarbonyl substituent —COX occupies either position 1 or position 2 of the naphthalene nucleus;

X is chlorine or bromine;

R is lower-alkyl or benzyl; or both R groups together constitute a methylene group bonded to both oxygen atoms, and Q is hydrogen or methyl.

These acid chlorides are useful as intermediates in the preparation of amides having the formula XVIII hereinabove.

In another composition aspect, the invention resides in the chemical compounds having the formula XXX hereinbelow:

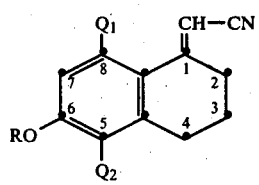    XXX wherein R is lower-alkyl, and $Q_1$ and $Q_2$ are each hydrogen or OR, provided that $Q_1$ and $Q_2$ are not simultaneously hydrogen or OR.

These nitriles are useful as intermediates in the preparation of nitriles having the formula XIX hereinabove, wherein the side chain represented by —$CR_1R_2CN$ occupies position 1 of the naphthalene nucleus, and $R_1$ and $R_2$ are hydrogen.

A further composition aspect of the invention resides in the chemical compounds having the formula XXXI hereinbelow:

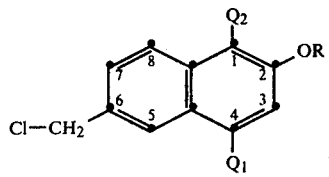    XXXI wherein $Q_1$ and $Q_2$ are each hydrogen or OR provided that $Q_1$ and $Q_2$ are not simultaneously hydrogen or OR, and R is lower-alkyl.

These halides are valuable intermediates in the preparation of the nitriles of formula XIX hereinabove, wherein the side chain represented by —$CR_1R_2CN$ occupies position 2 of the naphthalene nucleus and $R_1$ and $R_2$ are hydrogen.

In a further composition aspect, the invention resides in the chemical compounds having the formula XXXII hereinbelow:

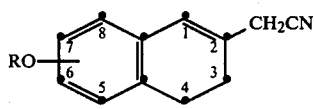    XXXII wherein the RO substituent occupies either position 6 or position 7 of the naphthalene nucleus; and R is lower-alkyl or benzyl.

These nitriles are useful as intermediates in the preparation of the compounds of formula XXIII hereinabove wherein $R_2$ and $R_3$ are hydrogen.

In still another composition aspect, the invention resides in the chemical compounds having the formula XXXIII hereinbelow:

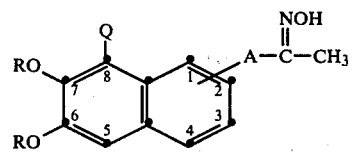    XXXIII wherein the side chain represented by

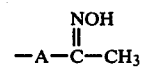

occupies either position 1 or position 2 of the naphthalene nucleus;

R is lower-alkyl, benzyl; or both R groups together constitute a methylene group bonded to both oxygen atoms, Q is hydrogen or methyl, and A is carbonyl or CHOH.

These oximes are useful as intermediates in the preparation of the hydroxy amines of formula XXV hereinabove.

The compounds XXXIII wherein A is carbonyl are useful as intermediates in the preparation of oximes XXXIII wherein A is CHOH.

Another composition aspect of the invention resides in the chemical compounds having the formula XXXIV hereinbelow:

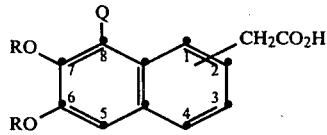    XXXIV wherein the side chain represented by —$CH_2CO_2H$ occupies either position 1 or position 2 of the naphthalene nucleus;

R is hydrogen, lower-alkyl or benzyl; or both R groups together constitute a methylene group bonded to both oxygen atoms, and Q is hydrogen or methyl.

The acids (XXXIV) are useful as intermediates in the preparation of the corresponding acid chlorides of formula XXVI hereinabove.

The acids are also useful as intermediates in the preparation of the alcohols of formula XXVII hereinabove.

The acids XXXIV wherein R is hydrogen are useful as intermediates in the preparation of the acids of formula XXXIV wherein R is lower-alkyl or benzyl, or wherein both R groups together constitute a methylene group bonded to both oxygen atoms.

The invention, in another composition aspect, resides in the chemical compounds having the formula XXXV hereinbelow:

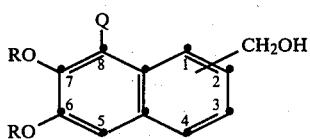

XXXV wherein the hydroxymethyl substituent occupies either position 1 or position 2 of the naphthalene nucleus, and R is lower-alkyl or benzyl; or both R groups together constitute a methylene group bonded to both oxygen atoms, and Q is hydrogen or methyl.

These alcohols are useful as intermediates in the preparation of the chloromethyl compounds of formula XXVIII hereinabove.

A further composition aspect of the invention resides in the chemical compounds having the formula XXXVI hereinbelow:

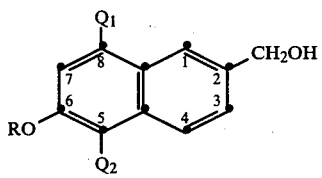

XXXVI wherein $Q_1$ and $Q_2$ are each hydrogen or OR, provided that $Q_1$ and $Q_2$ are not simultaneously hydrogen or OR, and R is lower-alkyl.

These alcohols are useful as intermediates in the preparation of the halides of formula XXXI hereinabove.

Another composition aspect of the invention resides in the thiomorpholides having the formula XXXVII hereinbelow:

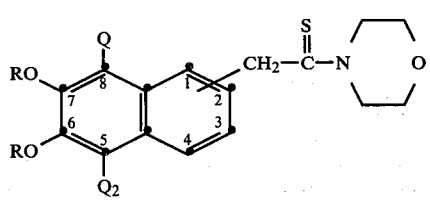

XXXVII wherein the side chain represented by

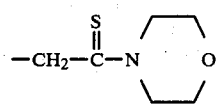

occupies either position 1 or position 2 of the naphthalene nucleus;

R is lower-alkyl or benzyl; or both R groups together constitute a methylene group bonded to both oxygen atoms, and Q is hydrogen or methyl.

These thiomorpholides are useful as intermediates in the preparation of the carboxylic acids of formula XXXIV hereinabove.

In another composition aspect, the invention resides in the chemical compounds having the formula XXXVIII hereinbelow:

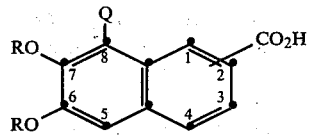

XXXVIII wherein the carboxyl group occupies either position 1 or position 2 of the naphthalene nucleus;

R is lower-alkyl or benzyl; or both R groups together constitute a methylene group bonded to both oxygen atoms, and Q is hydrogen or methyl provided that when the carboxyl group occupies position 2, Q is not hydrogen.

These acids are useful as intermediates in the preparation of the corresponding acid chlorides of formula XXIX as well as the alcohols of formula XXXV hereinabove.

In another composition aspect, the invention resides in the chemical compounds having the formula XXXIX hereinbelow:

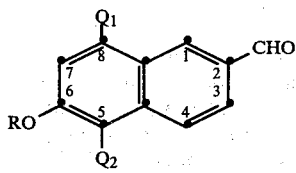

XXXIX wherein $Q_1$ and $Q_2$ are each hydrogen or OR provided that $Q_1$ and $Q_2$ are not simultaneously hydrogen or OR, and R is lower-alkyl.

The aldehydes XXXIX are useful as intermediates in the preparation of the alcohols of formula XXXVI hereinabove.

A further composition aspect of the invention resides in the chemical compounds having the formula XL hereinbelow:

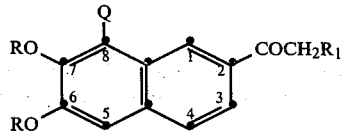

XL wherein R is lower-alkyl or benzyl; or both R groups together constitute a methylene group bonded to both oxygen atoms;

Q and $R_1$ are independently hydrogen or methyl, and the side chain represented by —$COCH_2R_1$ occupies either position 1 or position 2 of the naphthalene nucleus, provided that when said side chain occupies position 2, Q is not hydrogen.

These ketones are useful as intermediates in the preparation of the thiomorpholides of formula XXXVII hereinabove. They are also useful as intermediates in the preparation of the haloketones of formula XV. The ketones XL are also useful as intermediates in the preparation of the oximes of formula XXXIII. The ketones of formula XL are also useful as intermediates in the preparation of the naphthoic acids of formula XXXVIII hereinabove.

Another composition aspect of the invention resides in the chemical compounds having the formula XLI hereinbelow:

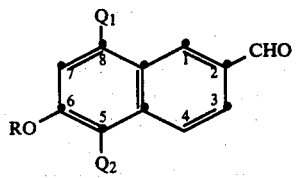

XLI wherein $Q_1$ and $Q_2$ are each hydrogen or OR provided that $Q_1$ and $Q_2$ are not simultaneously hydrogen or OR, and R is lower-alkyl.

These aldehydes are useful as intermediates in the preparation of the aldehydes of formula XXXIX hereinabove.

In another composition aspect, the invention resides in the chemical compounds having the formula XLII hereinbelow:

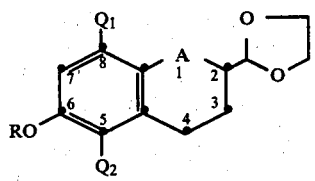

XLII wherein $Q_1$ and $Q_2$ are each hydrogen or OR provided that $Q_1$ and $Q_2$ are not simultaneously hydrogen or OR;

R is lower-alkyl, and

A is carbonyl or CHOH.

The compounds XLII wherein A is carbonyl are useful as intermediates in the preparation of the corresponding alcohols XLII wherein A is CHOH which are in turn useful as intermediates in the preparation of the aldehydes of formula XLI hereinabove.

In one of its process aspects, the invention sought to be patented resides in the chemical process which comprises cleaving the RO-substituted compounds of formulas VII, IX, X (A is $CH_2$ or C=O), XI and XII (A is $CH_2$ or C=O) to produce the corresponding hydroxy-substituted compounds having the formulas I ($R=R_1=H$; A is C=O, a direct linkage or $CR_5R_6$ as defined hereinabove), III ($R=R_1=H$), IV ($R=R_1=H$; A is $CH_2$ or C=O), V (R=H) and VI ($R_1=H$; A is $CH_2$ or C=O), respectively.

In another process aspect, the invention resides in the chemical process which comprises reducing the aminoketones of formula I wherein A is C=O and formula VI wherein A is C=O to produce respectively the aminoalcohols I wherein A is CHOH and VI wherein A is CHOH.

Also considered within the ambit of this process aspect of the invention is the chemical process which comprises simultaneous reduction and debenzylation of the aminoketones having one or two nitrogen-bound benzyl groups, I (A is C=O and either one of or both $R_4$ and $R_5$=benzyl) to produce the corresponding debenzylated aminoalcohols I wherein A is CHOH, and containing no nitrogen-bound benzyl substituents. This process is of particular advantage where early preparative steps require a suitably protected amine function but where the desired final product is a primary or secondary amine.

Another process aspect of the invention resides in the chemical process which comprises the simultaneous hydrolysis, decarboxylation and R-O cleavage of a malonic ester derivative of formula VIII to produce the amino acid derivative having the formula II.

A further process aspect of the invention resides in the chemical process which comprises esterifying the hydroxy-substituted compounds of formulas I ($R=R_1=H$; A is C=O, a direct linkage or $CR_6R_7$ as defined hereinabove), II ($R=R_1=H$), III($R=R_1=H$), IV ($R=R_1=H$), V (R=H), VI ($Q=R_1=H$), and VI (Q=OR, $R=R_1=H$; A is $CH_2$ or C=O) to produce the corresponding mono or diesters having respectively the formulas I (A is C=O, a direct linkage or $CR_6R_7$ as defined hereinabove), II, III, IV and VI (Q=OR; A is $CH_2$ or C=O) wherein in each of the said formulas at least one of R and $R_1$ is lower-alkanoyl or aroyl while the other is hydrogen, or wherein both R and $R_1$ are lower-alkanoyl or aroyl; and also V and VI (Q=H) wherein R is lower-alkanoyl or aroyl.

In another process aspect, the invention resides in the chemical process which comprises reducing the RO-substituted aminoketones of formulas VII and X wherein A is carbonyl to produce the compounds having formulas VII and X respectively wherein A is methylene.

Also considered within the scope of the process aspect of this invention is the simultaneous reduction and N-debenzylation of the aminoketones bearing one or two N-benzyl groups, e.g., VII (A is C=O; one of or both $R_3$ and $R_4$=benzyl) and X (A is C=O, one of or both $R_2$ and $R_3$=benzyl) to produce respectively the amines of formulas VII (A is methylene) and X (A is methylene) containing no nitrogen-bound benzyl groups. This process is advantageous where early preparative steps require a protected amine but where the desired final product is a primary or secondary amine.

The invention, in another process aspect, resides in the chemical process which comprises reducing the compounds having formulas VII and X wherein A is CH-OH to produce the compounds of formulas VII and X respectively wherein A is methylene.

As will be apparent to one skilled in the art, reduction of the aminoketones (VII and X; A is C=O) to the naphthalenealkylamines (VII and X; A is $CH_2$) proceeds through the intermediacy of the aminoalcohols (VII and X; A is CHOH) and therefore the process which comprises reducing said aminoketones (VII and X; A is C=O) to the corresponding aminoalcohols (VII and X; A is CHOH) is also within the ambit of the instant invention.

In another process aspect, the invention resides in the chemical process which produces RO-substituted aminoketones of formula VII wherein A is carbonyl by reacting the RO-substituted haloketones of formula XV with ammonia or primary or secondary amines having the formula XLIII hereinbelow:

XLIII wherein a and b are independently hydrogen, lower-alkyl, benzyl, aryl, or -Nab is pyrrolidino, piperidino, hexamethyleneimino, morpholino, or any of these having from one to two lower-alkyl substituents.

A further process aspect of the invention resides in the chemical process which comprises halogenating RO-substituted acetonaphthones having the formula XL hereinabove to produce the haloketones of formula XV hereinabove.

In another process aspect, the invention provides the chemical process which comprises alkanoylating the di(RO)naphthalenes having the formula XLIV hereinbelow:

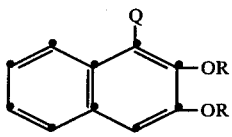
XLIV wherein R is lower-alkyl or benzyl; or both R groups together constitute a methylene group bonded to both oxygen atoms, and Q is hydrogen or methyl, to produce the acetonaphthones of formula XL hereinabove.

In another process aspect, the invention resides in the chemical process which comprises reducing the haloamine derivatives of formula XIII to produce amines having the formula VII wherein A is methylene.

Another process aspect of the invention resides in the chemical process which comprises reducing the naphthaleneacetamides of formula XIV to produce the corresponding amines of formula VII wherein A is methylene and $R_1$ is hydrogen.

The invention, in another process aspect, resides in the chemical process which comprises reacting the naphthaleneacetyl halides of formula XXVI with ammonia or primary or secondary amines of formula XLIII to produce the naphthaleneacetamides of formula XIV.

In another process aspect, the invention resides in the chemical process which comprises converting the naphthaleneacetic acids of formula XXXIV to the corresponding acid chlorides of the formula XXVI.

A further process aspect of the invention resides in the chemical process which comprises hydrolyzing the thiomorpholides of the formula XXXVII to produce the naphthaleneacetic acids of formula XXXIV.

Another process aspect of the invention resides in the chemical process which comprises converting the di(-RO)acetonaphthones of formula XL ($R_1$=H) to the thiomorpholides of formula XXXVII.

In another process aspect, the invention resides in the chemical process which comprises reacting the halides or tosylates of formula XVI with ammonia or primary or secondary amines of formula XLIII to produce 6,7-di(RO)-2-naphthaleneethylamines of formula VII wherein A is methylene and $R_1$ is hydrogen.

The invention, in another process aspect, resides in the chemical process which comprises reducing a 6,7-di(RO)naphthaleneacetonitrile of formula XVII to produce the corresponding amine of formula VII wherein:
A is $CR_4R_5$ as defined hereinabove, and
$R_1$ is hydrogen.

Another process aspect of the invention resides in the chemical process which comprises reducing the 6,7-di(-RO)naphthamides of formula XVIII to produce the corresponding 6,7-di(RO)naphthalenemethylamines of formula VII wherein A is a direct linkage.

A further process aspect of the invention resides in the chemical process which comprises reacting chloromethyl-2,3-di(RO)naphthalenes of the formula XXVIII with sodio diethyl acetamidomalonate to produce the malonic ester derivatives having the formula VIII.

The invention, in another of its process aspects, resides in the chemical process which comprises reducing the dialkoxynaphthaleneacetonitriles having the formula XIX to produce the corresponding amines of formula IX.

In another process aspect, the invention resides in the chemical process which comprises reducing the nitro olefins of formula XX to produce the 4,8-di(RO)naphthaleneethylamines having the formula X wherein $R_1$, $R_2$ and $R_3$ are hydrogen, and A is methylene.

A further process aspect of the invention resides in the chemical process which comprises reducing the RO-2-naphthaleneacetamides of formula XXII to produce the corresponding amines having the formula XI wherein $R_2$ and $R_3$ are hydrogen.

The invention, in another process aspect, resides in the chemical process which comprises reducing the RO-2-naphthaleneacetonitriles having the formula XXIII to produce the corresponding amines of formula XI wherein $R_3$ is hydrogen.

Another process aspect of the invention resides in the chemical process which comprises reducing the amines having the formula XXIV to produce the amines of formula XI wherein $R_1$ and $R_2$ are hydrogen and $R_3$ is methyl.

In another process aspect, the invention provides a chemical process which comprises reacting the amines of formulas VII (A—$CHR_1NR_3R_4$ at position 2; A is $CR_4R_5$; $R_2$=$R_3$=$R_4$=$R_5$=H) and XI (RO at position 6; $R_1$=$R_2$=$R_4$=$R_5$=H) with a carbonyl compound of the formula XLV hereinbelow:

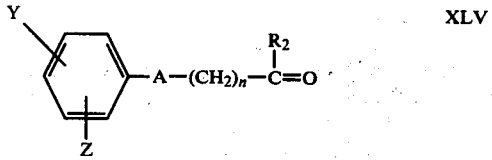
XLV wherein $R_2$, A, n, Y and Z have the same significance indicated hereinabove, in the presence of a reducing agent to produce the substituted amines of formula XII.

Preparation of Final Products

Certain of the final products of the invention, namely the compounds of formula I wherein R=$R_1$=H and A is C=O, a direct linkage, or $CR_5R_6$ as defined hereinabove, the compounds of formula III wherein R=$R_1$=H, the compounds of formula IV wherein $R=R_1=H$; the compounds of formula V wherein $R=H$ and the compounds of formula VI wherein $R=R_1=H$; A is C=O or $CH_2$, are conveniently prepared by cleavage of the corresponding RO-substituted compounds of formulas VII, IX, X (A is C=O or $CH_2$), XI and XII (A is C=O or $CH_2$), respectively. This cleavage is effected through the agency of acidic reagents such as, for example, hydrogen chloride, hydrogen bromide, hydrogen iodide; boron tribromide, aluminum chloride or aluminum bromide. In the case where RO is benzyloxy, cleavage can also be effected with trifluoroacetic acid or by catalytic hydrogenolysis using hydrogen and a suitable catalyst such as, for example, palladium-on-carbon or Raney nickel. A preferred mode of carrying out the cleavage reaction consists of heating the RO-substituted compound with hydrogen chloride or hydrogen bromide in an aqueous medium at a temperature of from 80° C. to 130° C., preferably at the reflux temperature of the reaction mixture, for a period of from one-half to three hours.

It will be obvious that the above-described cleavage methods, as applied to the RO groups bound to the naphthalene ring, also effect similar cleavage of RO groups which may be bound at other points in the molecule. For example, compounds of the formula XII (A is $CH_2$ or C=O) wherein Y and/or Z is methoxy are converted to the compounds of formula VI (A is $CH_2$ or C=O) wherein Y and/or Z is hydroxy.

The amino alcohols of formula I wherein A is CH—OH are prepared by reducing the corresponding aminoketones I wherein A is carbonyl. The reduction by catalytic hydrogenation can be effected in the presence of a noble metal catalyst such as platinum or palladium. The reaction is conveniently carried out by shaking a solution of the aminoketone in the form of its acid-addition salt in DMF at 20°-60° C. under a hydrogen pressure of from 20–50 psi in the presence of an effective amount of palladium-on-carbon. The hydrogenation is continued until the theoretical amount of hydrogen is absorbed. A hydrogenation time of six hours or less is generally satisfactory. This same reductive procedure also effects reduction of the ketones VI (A is C=O) to the corresponding alcohols VI (A is CHOH).

It will be appreciated that benzyl substituents attached to the nitrogen atom of the starting amino ketone I (A is C=O; either one of or both $R_4$ and $R_5$=benzyl) are cleaved during the above-described catalytic hydrogenation, with the additional absorption of one equivalent of hydrogen per benzyl group.

The amino acid derivatives of formula II hereinabove are obtained by treating the malonic ester derivatives of formula VIII hereinabove with a strong acid such as, for example, hydrochloric, hydrobromic or hydriodic acid in a suitable solvent as for example water or aqueous acetic acid at a temperature of from 80° C. to 130° C. for a period of from three to six hours. The reaction is conveniently carried out by heating together the malonic ester derivative of formula XIII with concentrated hydrochloric acid in acetic acid at the reflux temperature for about five hours. The product (II) is isolated as an acid-addition salt.

The esters of the invention having the formulas I (A is C=O, a direct linkage, or $CR_5R_6$ as defined hereinabove), II, III, IV and VI (Q is OR; A is $CH_2$ or C=O) wherein in each of the said formulas, at least one of R and $R_1$ is lower-alkanoyl or aroyl while the other is hydrogen or wherein both R and $R_1$ are lower-alkanoyl or aroyl, as well as V and VI (Q is hydrogen; A is $CH_2$ or C=O) wherein R is lower-alkanoyl or aroyl, are obtained by acylating the corresponding hydroxy compounds of formulas I (A is C=O, a direct linkage or $CR_5R_6$, as defined hereinabove; $R=R_1=H$), II ($R=R_1=H$), III ($R=R_1=H$), IV ($R=R_1=H$), VI (Q=OR; A is $CH_2$ or C=O; $R=R_1=H$), V (R=H) and VI (Q=R=H, A is $CH_2$ or C=O), with an appropriate acid halide in a strongly acidic medium at a temperature of from $-10°$ C. to 30° C. A reaction time of six hours or less is generally satisfactory. The reaction is conveniently carried out by reacting the appropriate hydroxy-substituted starting compound, in the form of its acid-addition salt, with an acid chloride in trifluoroacetic acid at 0° C. to 25° C. for about three to four hours.

It will be obvious that the above-described esterification of hydroxyl groups bound to the naphthalene ring will also effect esterification of other hydroxyl groups which may be present in the molecule. For example esterification of the compounds of formula VI wherein Q is OR; R and $R_1$ are hydrogen, and Y and/or Z are hydroxy will produce the esters of formula VI wherein R and $R_1$ as well as Y and/or Z are lower-alkanoyloxy or aroyloxy.

Preparation of Intermediates

The RO-substituted naphthalenealkylamines having formulas VII and X wherein A is methylene are obtained by catalytic hydrogenation of the corresponding ketones of formulas VII and X wherein A is carbonyl. The reduction is conveniently carried out by shaking a solution of said ketone in the form of its acid-addition salt in a suitable solvent as for example dimethylformamide or aqueous acetic acid, at 20° C. to 80° C. under a hydrogen pressure of from 20–50 psi in the presence of a strong acid as, for example, hydrochloric, and a noble metal catalyst such as palladium. The hydrogenation is continued until the theoretical amount of hydrogen is absorbed. A hydrogenation time of fifteen hours or less is generally satisfactory.

The aminoketones of formula VII and X (A is carbonyl) having one or two benzyl substituents bound to the nitrogen atom undergo concomitant debenzylation under the above-described reduction conditions. One additional mole of hydrogen is absorbed per benzyl group.

The above reaction conditions are also effective in reducing the alkoxy-substituted aminoalcohols of formulas VII and X wherein A is CHOH to the corresponding alkoxy-substituted naphthalenealkylamines of formulas VII and X wherein A is methylene.

It will be apparent that the above-described catalytic reduction of either the aminoketones (VII and X wherein A is carbonyl) or the aminoalcohols (VII and X wherein A is CHOH) wherein R is benzyl proceeds with cleavage of the benzyl groups to give the corresponding hydroxy-substituted compounds of formulas I (A is methylene) and IV wherein R and $R_1$ are hydrogen.

The RO-substituted aminoalcohols of formulas VII and X wherein A is CHOH are obtained by reducing the corresponding aminoketones of formulas VII and X wherein A is carbonyl with an appropriate reducing agent in a suitable solvent as for example lithium aluminum hydride in tetrahydrofuran, ether or dioxane; diborane in tetrahydrofuran or diglyme or by hydrogenation in the presence of a noble metal catalyst such as palladium or platinum. The reaction is conveniently carried out by treating said aminoketones with lithium aluminum hydride in refluxing tetrahydrofuran for from five to twenty hours. Alternatively, the reduction is effected by shaking a solution of the aminoketone in the form of its acid-addition salt in a suitable solvent as for example dimethylformamide, at 20° C. to 50° C. under a hydrogen pressure of from 20-50 psi in the presence of a noble metal catalyst such as palladium. The hydrogenation is continued until the theoretical amount of hydrogen is absorbed. A hydrogenation time of six hours or less is generally satisfactory.

It will be apparent that catalytic reduction of the aminoketones of formula VII (A is carbonyl) wherein R is benzyl proceeds with cleavage of the benzyl groups to give the hydroxy-substituted aminoalcohols of formula I wherein A is CHOH, and R and $R_1$ are hydrogen. Accordingly, when it is desirable to prepare the RO-substituted aminoalcohols VII or X (A is CHOH) wherein R is benzyl a chemical reduction procedure is employed.

Since the aminoketones (VII and X wherein A is carbonyl) are reduced to the corresponding aminoalcohols (VII and X wherein A is CHOH) which in turn are reduced to the amines (VII and X wherein A is methylene) it is apparent that the reduction of the aminoketones (VII and X wherein A is carbonyl) to the amines (VII and X wherein A is methylene) may optionally be carried out either in a single process or in a stepwise procedure.

The aminoketones having the formulas VII and X wherein A is carbonyl are conveniently prepared by treating the haloketones of formulas XV and XXI in acetonitrile with an excess of ammonia or a primary or secondary amine at from −30° C. to 90° C. for about two to twenty hours.

The haloketones of formulas XV and XXI are conveniently prepared by halogenating the appropriate acetonaphthones (XL and XLVI hereinbelow) with a halogen as for example chlorine or bromine in chloroform at approximately 25° C. for about two hours.

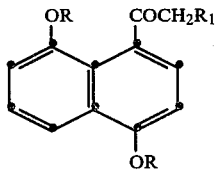

XLVI

R is lower-alkyl or benzyl, and
$R_1$ is hydrogen or methyl.

The di(RO)acetonaphthones of formula XL are conveniently prepared by treating the 2,3-di(RO)naphthalenes of formula XLIV hereinabove in an inert solvent as for example sym-tetrachloroethane or nitrobenzene, at a temperature of about 0° C. to ambient temperatures, with an appropriate acid halide, e.g., acetyl chloride or propionyl chloride in the presence of a Lewis acid such as aluminum chloride for a period of from one to three hours. The reaction yields both the 1- and the 2-isomer.

The di(RO)acetonaphthones of formula XLVI are a known class of compounds prepared by reacting lower-alkanoyl halides with 1,5-di(RO)naphthalenes under Friedel-Crafts conditions.

Alternatively the haloketones of formulas XV and XXI are obtained by reacting the appropriate di(RO)-naphthalenes, e.g., XLIV and 1,5-di(RO)naphthalene with α-haloalkanoyl halides as for example chloroacetyl chloride, bromoacetyl bromide, α-bromopropionyl bromide and the like in the presence of a Lewis acid catalyst such as aluminum chloride or aluminum bromide in an appropriate solvent as for example dichloromethane or chloroform. The reaction is conveniently carried out by treating a di(RO)naphthalene in dichloromethane with the appropriate α-chloroalkanoyl chloride in the presence of aluminum chloride at approximately 25° C. for about 24 to 48 hours.

The α-iodoketones (XV and XXI, X=I) are obtained by reacting the corresponding chlorides or bromides with sodium iodide in refluxing acetone.

The di(RO)naphthalenes of formulas XLIV and 1,5-di(RO)naphthalenes are known classes of compounds prepared by the classical Williamson ether synthesis from the appropriate naphthalenediols and lower-alkyl halides.

The compounds of formula VII wherein A is methylene are also prepared by catalytic hydrogenation of the haloamines of formula XIII. The reaction is conveniently carried out by shaking a solution of the haloamine (XIII), in the form of its acid-addition salt, in dimethylformamide at approxiately 25° C. under a hydrogen pressure of from 22-50 psi in the presence of an effective amount of palladium-in-carbon. The hydrogenation is continued until the theoretical amount of hydrogen is absorbed. A hydrogenation time of six hours or less is generally satisfactory.

It will be appreciated that the above-described catalytic reduction of haloamines of formula XIII wherein R is benzyl will also effect concomitant debenzylation to produce the hydroxy-substituted amines of formula I wherein A is methylene, and R and $R_1$ are hydrogen.

The haloamines of formula XIII are obtained by treating the corresponding hydroxyamines (VII wherein A is CHOH; and XXV) with a thionyl halide in refluxing chloroform for about one hour.

The hydroxyamines of formula XXV are obtained by catalytic hydrogenation of the oximino ketones XXXIII (A is C=O) or the oximino alcohols XXXIII (A is CHOH) in ethanol at about 25° C. to 65° C., under a hydrogen pressure of 20-50 psi in the presence of an effective amount of palladium and an excess of hydrochloric acid. The hydrogenation is continued until the theoretical amount of hydrogen is absorbed. A hydrogenation time of six hours or less is generally satisfactory.

It will be apparent that catalytic reduction of either the oximino ketones (XXXIII; A is carbonyl) or the oximino alcohols (XXXIII; A is CHOH) wherein R is benzyl results in the cleavage of the benzyl groups to produce the hydroxy-substituted compounds XXV wherein R is replaced by hydrogen. Accordingly the hydroxyamines of formula XXV wherein R is benzyl are prepared by reduction of the oximino ketones XXXIII (A is carbonyl) or the oximino alcohols XXXIII (A is CHOH) with a suitable chemical reducing agent in an appropriate solvent, e.g., lithium aluminum hydride in ether, dioxane or tetrahydrofuran.

The oximino alcohols of formula XXXIII (A is CHOH) are prepared by reduction of the corresponding oximino ketones XXXIII (A is C=O) with an appropriate chemical reducing agent in an appropriate solvent, e.g., sodium borohydride in a lower-alkanol, or diglyme, optionally in the presence of an alkali metal hydroxide at a temperature of about 0° C. to 50° C. The reduction is conveniently carried out by treating said oximino ketone in ethanol containing sufficient sodium hydroxide to dissolve the oxime with sodium borohydride at ambient temperatures for about three hours.

The oximino ketones XXXIII (A is C=O) are obtained by treating the di(RO)acetonaphthones of formula XL ($R_1$=$CH_3$), in ether or benzene or a mixture thereof, with an alkyl nitrite, e.g., butyl nitrite, amyl nitrite, or iso-amyl nitrite in the presence of an acid such as hydrogen chloride or hydrogen bromide. The reaction is conveniently carried out by treating said oximino ketone in a refluxing mixture of ether and benzene with a slight molar excess of amyl nitrite in the presence of hydrogen chloride for about five hours.

The di(RO) compounds of formula VII wherein A is methylene and $R_1$ is hydrogen are obtained by reducing the di(RO)naphthaleneacetamides of formula XIV with a suitable chemical reducing agent in an appropriate solvent, e.g., diborane in tetrahydrofuran or diglyme; or lithium aluminum hydride in tetrahydrofuran, ether or dioxane, at 0° C. to 65° C. for from about one to about 24 hours. The reaction is conveniently carried out by heating said amide with diborane in tetrahydrofuran at the reflux temperature for from about six to about eight hours.

The di(RO)naphthaleneacetamides of formula XIV are obtained by reacting the corresponding acid halides of formula XXVI with an excess of an appropriate amine of formula XLIII in a suitable solvent such as ether, benzene or chloroform or in a heterogeneous mixture of one of these solvents with water at from about 0° C. to ambient temperatures. The reaction is conveniently carried out by treating an aqueous solution of at least two equivalents of the amine (XLIII) with an ethereal solution of the acid chloride (XXVI) with ice-bath cooling.

The di(RO)naphthaleneacetyl chlorides of formula XXVI are prepared from the corresponding carboxylic acids (XXXIV) by reaction in a suitable solvent, e.g., benzene, chloroform or ethylene dichloride with an appropriate halogenating agent such as thionyl halide or phosphorous oxyhalide. The reaction is conveniently carried out by reacting the carboxylic acids (XXXIV) in chloroform with an excess of thionyl halide at 25° C. to 50° C. for about one to two hours.

The di(RO)naphthalaneacetic acids XXXIV are obtained by treating the thiomorpholides of formula XXXVII with refluxing aqueous sodium hydroxide for from about five to about ten hours.

The thiomorpholides (XXXVII), in turn, are prepared by treating the appropriate di(RO)acetonaphthones XL ($R_1$=H) with sulfur in refluxing morpholine (optionally in the presence of an acid catalyst such as p-toluenesulfonic acid) for from about three to about ten hours.

Alternatively, the di(RO) compounds of formula VII wherein A is methylene and $R_1$ is hydrogen are obtained by reacting a halide or tosylate of formula XVI in a suitable solvent, e.g., a lower-alkanol, acetonitrile, tetrahydrofuran or dimethylformamide, with an appropriate amine of formula XLIII in the presence of an acid-acceptor, e.g., an alkali metal carbonate, or an excess of the amine XLIII. The reaction is conveniently carried out by treating a solution of at least two equivalents of said amine in dimethylformamide with a halide or tosylate (XVI) with ice-bath cooling.

The intermediates (XVI) are prepared from the corresponding alcohols (XXVII) by reaction with p-toluenesulfonyl chloride in pyridine with ice-bath cooling. The reaction produces a mixture of the chloride (XVI, X=Cl) and the tosylate (XVI, X is

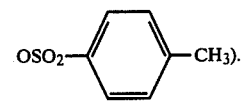

The naphthaleneethanols (XXVII) are prepared by reducing the naphthaleneacetic acids of formula XXXIV with a suitable chemical reducing agent in an appropriate solvent, e.g., lithium aluminum hydride in ether, tetrahydrofuran, or dioxane; or diborane in tetrahydrofuran or diglyme, at temperatures of from about 0° C. to about 80° C. for approximately one to eighteen hours. The reaction is conveniently carried out by treating said acid in tetrahydrofuran with lithium aluminum hydride on the steam bath for approximately one to two hours.

The di(RO) compounds of formula VII wherein A is $CR_4R_5$ and $R_1$ is H are obtained by reducing the naphthaleneacetonitriles of formula XVII with a suitable chemical reducing agent in a suitable solvent, e.g., lithium aluminum hydride in tetrahydrofuran, ether, or dioxane, or with hydrogen in the presence of a suitable catalyst such as Raney nickel in a solution of a lower-alkanol containing ammonia. The reaction is conveniently carried out by treating said nitrile XVII in tetrahydrofuran with lithium aluminum hydride at the reflux temperature for about two hours.

It is obvious that both of the above-described procedures will afford the primary amine (VII; A is $CR_4R_5$; $R_1$=$R_2$=$R_3$=H). In order to obtain secondary and tertiary amines, i.e., amines of formula VII wherein $R_2$ and $R_3$ are substituents other than hydrogen, the above-described method of hydrogenation over Raney nickel is used wherein ammonia is replaced by a primary or secondary amine bearing the desired substituents $R_2$ and $R_3$. Furthermore catalytic reduction of those naphthaleneacetonitriles (XVII) wherein R is benzyl will proceed with cleavage of the benzyl groups to give the hydroxy-substituted amines I (A is $CR_5R_6$, $R_2$=H) wherein R and $R_1$ are hydrogen.

The intermediate nitriles XVII ($R_1$=$R_2$=H) are conveniently prepared by treating the chloromethyl compounds of formula XXXVIII with sodium cyanide in dimethyl sulfoxide at temperatures of about 0° C. to ambient temperatures for about one-half to about seven hours.

The nitriles so produced may subsequently be treated with an appropriate amount of a methylating agent such as methyl iodide in dimethylformamide in the presence of an appropriate amount of a strong base, e.g., sodium hydride at about 20° C. to 85° C. for about one to three hours to afford the nitriles (XVII) wherein at least one of or both $R_1$ and $R_2$ are methyl.

The chloromethyl compounds XXVIII are conveniently prepared by treating the di(RO)naphthalenemethanols of formula XXXV in benzene with hydrogen chloride in the presence of sodium sulfate with ice-bath cooling.

The di(RO)naphthalenemethanols XXXV are prepared by reducing the naphthoic acids of formula XXXVIII using the procedure described hereinabove for the preparation of the naphthaleneethanols of formula XXVII.

The naphthoic acids of formula XXXVIII are obtained by oxidizing the acetonaphthones of formula XL ($R_1$=H) with a suitable hypohalite in alkaline solution. The reaction is conveniently carried out by treating said acetonaphthones with an excess of 5.25% sodium hypochlorite solution (Chlorox ®) in the presence of sodium hydroxide on the steam bath for one-half to about six hours.

The di(RO) compounds of formula VII wherein A is a direct linkage, and $R_1$ and $R_2$ are hydrogen are prepared by reducing the di(RO)naphthamides of formula XVII with a suitable chemical reducing agent in a suitable solvent, e.g., lithium aluminum hydride in tetrahydrofuran, ether, or dioxane; or diborane in tetrahydrofuran or diglyme at about 25° C. to 85° C. for about one-half to three hours. The reaction is conveniently carried out by treating said amide in refluxing tetrahydrofuran with lithium aluminum hydride for about one to about two hours.

The naphthamides of formula XVIII are prepared from the naphthoyl halides of formula XXIX using the procedure described hereinabove for the preparation of the naphthaleneacetamides (XIV).

The intermediate naphthoyl halides XXIX are prepared from the corresponding naphthoic acids XXXVIII using the procedure described hereinabove for the preparation of the naphthaleneacetyl halides (XXVI).

The malonic ester derivative VIII is obtained by reacting an alkali-metal salt, e.g., sodium salt, of diethyl acetamidomalonate in a dipolar aprotic solvent, e.g., dimethyl sulfoxide or dimethylformamide, with a chloromethyl-2,3-di(RO)naphthalene of the formula XXVIII (Q=H). The reaction is conveniently carried out by treating a solution of sodio diethyl acetamidomalonate in dimethyl sulfoxide with said chloromethyl compound at about ambient temperature for from about twelve to about twenty-four hours.

The dialkoxynaphthalenealkylamines having the formula IX are prepared by reducing the nitriles of formula XIX with a suitable reducing agent as for example lithium aluminum hydride, or hydrogen in the presence of a suitable catalyst such as Raney nickel. The reaction is conveniently carried out by shaking a solution of nitrile XIX and ammonia or a primary or secondary amine in methanol at 20° C. to 50° C. under a hydrogen pressure of 20–50 psi in the presence of Raney nickel. The hydrogenation is continued until the theoretical amount of hydrogen is absorbed.

The dialkoxynaphthalene-1-acetonitriles of formula XIX ($CR_1R_2CN$ at position 1; $R_1$=$R_2$=H) are prepared by oxidizing the unsaturated nitriles of formula XXX. The reaction is conveniently carried out by treating a solution of nitrile XXX in refluxing carbon tetrachloride with a molar equivalent of N-bromosuccinimide for about two to about four hours followed by treatment with a base such as an alkali metal hydroxide, carbonate or bicarbonate, or a tertiary amine, e.g., N,N-dimethylaniline.

The unsaturated nitriles of formula XXX are prepared by treating a glyme solution of the tetralones having the formula XLVII ($Q_1$, $Q_2$, and R have the meaning given under formula XXX) hereinbelow:

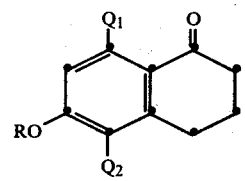

XLVII with diethyl phosphoroacetonitrile and sodium hydride at about 20° C. to 30° C. for approximately one to twenty-four hours.

The tetralones XLVII are a known class of compounds obtained from readily available materials.

The dialkoxynaphthalene-2-acetonitriles of formula XIX ($CR_1R_2CN$ at position 2; $R_1$=$R_2$=H) are prepared from the chloromethyldialkoxynaphthalenes of formula XXXI using the procedure described hereinabove for the preparation of the 6,7-dialkoxynaphthaleneacetonitriles of formula XVII.

The intermediate chloromethyl compounds XXXI are obtained from the corresponding hydroxymethyl compounds XXXVI using the procedure described hereinabove for the preparation of the chloromethyl derivatives XXVIII.

The hydroxymethyl compounds XXXVI are prepared by reducing the corresponding naphthaldehydes of formula XXXIX using a procedure similar to that described hereinbelow for the preparation of the hydroxy acetals of formula XLII wherein A is CHOH.

The naphthaldehydes of formula XXXIX are obtained by oxidizing the dihydronaphthaldehydes XLI. The reaction is conveniently carried out by irradiating a solution of said dihydronaphthaldehyde and N-bromosuccinimide in carbon tetrachloride at the reflux temperature for a period of from about three to about five hours.

The dihydronaphthaldehydes (XLI) in turn, are obtained by the simultaneous dehydration-hydrolysis of the hydroxy acetals of formula XLII (A is CHOH). The reaction is conveniently carried out by treating said hydroxy acetal in acetic acid with a mixture of water and concentrated sulfuric acid at ambient temperatures for about two hours.

The hydroxy acetals XLII (A is CHOH) are obtained by reducing the corresponding ketones XLII (A is C=O) with a suitable chemical reducing agent in an appropriate solvent such as lithium aluminum hydride in tetrahydrofuran, ether or dioxane; or sodium borohydride in a lower-alkanol, at a temperature of about 0° C. to 50° C. for a period of from about one to about three hours. The reaction is conveniently carried out by treating said ketone with excess sodium borohydride in 2-propanol at about ambient temperature for approximately two hours.

The keto acetals XLII (A is C=O) are obtained by acetalization of the hydroxymethylene ketones of formula XLVIII ($Q_1$, $Q_2$ and R have the meaning stated hereinabove under formula XLII) hereinbelow:

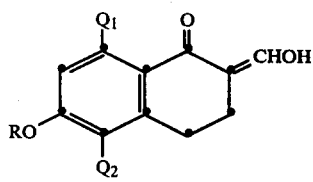

XLVIII

The reaction is conveniently carried out by treating a benzene solution of said hydroxymethylene ketone with excess ethylene glycol in the presence of an acid catalyst such as p-toluenesulfonic acid and removing the water formed therefrom by azeotropic distillation.

The hydroxymethylene ketones XLVIII are a known class of compounds prepared from readily available materials.

The 4,8-di(RO) compounds of formula X wherein A is $CH_2$, and $R_1=R_2=R_3=H$ are prepared by reducing the nitroolefins of formula XX with a suitable reducing agent in a suitable solvent, e.g., lithium aluminum hydride in tetrahydrofuran, ether, or dioxane; or with hydrogen in the presence of a suitable noble metal catalyst such as palladium or platinum. The reduction is conveniently carried out by treating the nitroolefin XX in refluxing tetrahydrofuran with excess lithium aluminum hydride for about two to about six hours.

It will be apparent that catalytic reduction of the nitroolefin of formula XX wherein R is benzyl will result in cleavage of the benzyl groups producing the amines of formula IV ($R_2=R_3=R_4=H$) wherein R and $R_1$ are hydrogen.

The nitroolefins of formula XX are obtained by treating the 4,8-di(RO)-I-naphthaldehydes of formula XLIX (R=lower-alkyl or benzyl) hereinbelow:

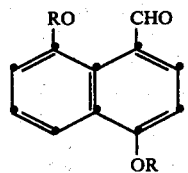
XLIX in refluxing acetic acid with an excess of nitromethane in the presence of ammonium acetate for about four to eight hours.

The aldehydes XLIX are a known class of compounds prepared from readily available materials.

The compounds of formula XI wherein $R_2=R_3=H$ are prepared by reducing the corresponding naphthaleneacetamides of formula XXII using either the procedure described hereinabove for the reduction of amides XIV or the procedure described for the reduction of amides XVIII.

The naphthaleneacetamides XXII are obtained from the naphthaleneacetyl chloride of formula L (R=lower-alkyl or benzyl, $R_1=H$ or $CH_3$) hereinbelow:

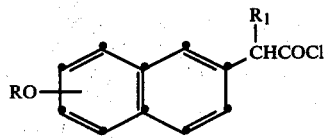
L using the procedure described hereinabove for the preparation of the naphthaleneacetamides of formula XIV.

The naphthaleneacetyl chlorides of formula L are a known class of compounds prepared from readily available materials.

Alternatively, the compounds of formula XI wherein $R_3=H$ are prepared from the corresponding nitriles XXIII using the procedure described hereinabove for the reduction of the nitriles of formula XIX.

It will be apparent that catalytic reduction of the nitriles XXIII wherein R is benzyl will result in cleavage of the benzyl group to produce the naphthols of formula V ($R_4=H$) wherein R is hydrogen.

The nitriles XXIII wherein one of or both $R_2$ and $R_3$ are methyl are obtained by methylating the unsubstituted nitriles XXIII ($R_2=R_3=H$) using the procedure described hereinabove for the methylation of the nitriles of formula XVII ($R_1=R_2=H$).

The intermediate nitriles XXIII wherein $R_2=R_3=H$ are prepared by dehydrogenating the corresponding dihydronaphthaleneacetonitriles XXXII. The reaction is conveniently carried out by heating a solution of the dihydro derivative in xylene to the reflux temperature in the presence of a noble metal catalyst such as palladium for about twenty to thirty hours.

The dihydronaphthaleneacetonitriles XXXII are prepared by reacting the tetralones of formula LI hereinbelow:

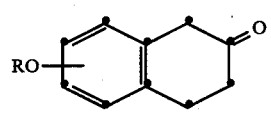
LI with diethylphosphonoacetonitrile using the procedure described hereinabove for the preparation of nitriles XXX.

The tetralones (LI) are a known class of compounds prepared from readily available materials.

Alternatively, the (RO)naphthalenealkylamines of formula XI wherein $R_1=R_2=H$; $R_3=CH_3$, are prepared by reducing the aminoketones XXIV (A is C=O) or the aminoalcohols XXIV (A is CHOH) using the procedures described above for the reduction of the aminoketones VII and X (A is C=O) and the reduction of the aminoalcohols VII and X (A is CHOH) to produce the amines VII and X (A is $CH_2$). As mentioned in these latter procedures, catalytic reduction of the aminoketones XXIV (A is C=O) or the aminoalcohols XXIV (A is CHOH) wherein R is benzyl will proceed with cleavage of the benzyl group to produce the naphthols of formula V ($R_2=R_3=H$) wherein R is hydrogen.

The aminoalcohols XXIV (A is CHOH) are prepared from the corresponding ketones (XXIV; A is C=O) using the procedure described hereinabove for the preparation of the aminoalcohols VII and X (A is CHOH).

The aminoketones XXIV (A is C=O) are obtained from the haloketones LII hereinbelow:

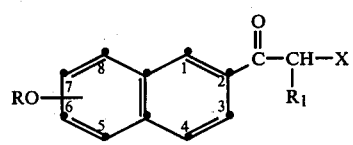
LII wherein the alkoxy group may occupy either position 6 or position 7 of the naphthalene nucleus;

R is lower-alkyl or benzyl;

$R_1$ is hydrogen or methyl, and

X is chlorine, bromine or iodine, using the procedure described hereinabove for the preparation of the aminoketones of formula VII (A is C=O) from the haloketones XV.

The haloketones LII are a known class of compounds prepared from readily available materials.

The alkoxy-substituted naphthalenealkylamines of formula XII are conveniently prepared by treating amines of formulas VII (A-CHR$_1$NR$_2$R$_3$ at position 2; A is CR$_4$R$_5$; R$_2$=R$_3$=R$_4$=R$_5$=H), and XI (RO at position 6; R$_1$=R$_2$=R$_4$=R$_5$=H), in the form of their acid-addition salts, in methanol with a carbonyl compound of formula XLV and sodium cyanoborohydride at a pH of 5.0 to 6.0 in the presence of molecular sieves having a pore diameter suitable for the absorption of water.

The carbonyl compounds of formula XLV are a known class of compounds, prepared from readily available materials.

As used hereinabove and throughout this specification, the terms lower-alkyl and lower-alkanoyl means such groups containing from one to four carbon atoms which can be arranged as straight- or branched-chains and, without limiting the generality of the foregoing, are illustrated by methyl, ethyl, propyl, isopropyl, butyl, sec-butyl, tert-butyl, and the like for lower-alkyl; and, acetyl, propionyl, butyryl, isobutyryl, and the like for lower-alkanoyl.

Aroyl means benzoyl or benzoyl substituted by from one to two lower-alkyl groups as defined hereinabove.

Aryl means phenyl or phenyl substituted by from one to two lower-alkyl groups.

The compounds of the invention having the formulas I-VII, IX-XIII, XXIV and XXV are useful both in the free base form and in the form of acid-addition salts, and both forms are within the purview of the invention. The acid-addition salts are simply a more convenient form for use, and in practice, use of the salt form inherently amounts to use of the base form. When the compounds of the invention represented by formulas I-VII, IX-XIII, XXIV and XXV are to be utilized for pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydriodic acid, nitric acid, phosphoric acid, sulfamic acid and sulfuric acid; and, organic acids such as cyclohexanesulfamic acid, methanesulfonic acid, ethanesulfonic acid, benzenesulfonic acid, p-toluenesulfonic acid, naponic acid (1,4-naphthalenedisulfonic acid), quinic acid, and the like, giving the hydrochloride, hydrobromide, hydriodide, nitrate, phosphate, sulfamate, sulfate, cyclohexanesulfamate, methanesulfonate, ethanesulfonate, benzenesulfonate, p-toluenesulfonate, naponate and quinate respectively.

The acid-addition salts of the bases of this invention are obtained by dissolving either or both of the base and the acid separately in water or an organic solvent and mixing the two solutions or by dissolving both the base and the acid together in water or an organic solvent. The resulting acid-addition salt is isolated by filtration, if it is insoluble in the reaction medium or by concentration of the solution or dilution of the solution with a solvent in which the acid-addition salt is insoluble or only sparingly soluble, or by evaporation of the reaction medium to leave the acid-addition salt as a residue.

Although medicinally acceptable salts of said basic compounds are preferred by pharmaceutical purposes, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

In standard biological test procedures the compounds of formulas I-VII and XI have been found to possess cardiotonic activity and are useful as cardiotonic agents. The efficacy of these compounds was judged, in vitro, on the basis of percent increase in contractile force in isolated cat atria and papillary muscle, and, in vivo, on the basis of percent increase in cardiac contractile force in the intact anesthetized dog.

The in vitro test procedures used are described as follows: Male cats weighing from 0.8 to 1.5 kg. were anesthetized with α-chloralose (80 mg./kg. i.p.). The chest was opened, the heart excised and the two atria dissected. A silk suture was tied to each of two opposite sides of the right atrium. One side of the atrium was tied to a glass rod and then mounted in a 50 ml. organ bath filled with Tyrode's solution. The second suture was attached to a force displacement transducer and the tension on the atrium was adjusted to 1.5±0.5 grams. The transducer was then connected to a Grass polygraph and the force and rate of atrial contraction was recorded continuously. The left atrium was treated similarly using silver wire instead of silk sutures. The silver wire also served as a stimulating electrode. Both atria were mounted in the same bath. The right atrium was beating spontaneously due to the presence of the sinoatrial node, while the left atrium was stimulated electrically at a rate of 3 beats/sec. by suprathreshold rectangular pulses of 5 millisecond duration. The Tyrode's solution bathing the atria was of the following composition (in mM): NaCl 136.87, KCl 5.36, NaH$_2$PO$_4$ 0.41, CaCl$_2$ 1.80, MgCl$_2$6H$_2$O 1.05, NaHCO$_3$ 11.90, glucose 5.55 and EDTA 0.04. The solution was equilibrated with a gas mixture consisting of 95% O$_2$ and 5% CO$_2$. The preparation was left to equilibrate for one hour before any drug was added. The bathing fluid was changed 3 to 4 times during the equilibration time. At the end of equilibration period, the drug dissolved in a vehicle or the vehicle alone was added to the tissue bath and the full response recorded. When the response reached a maximum it was abolished by 3 washes at 10 min. intervals or until pre-drug values of force of contraction were reached. A dose response study of at least 3 doses was done in the same preparation.

Male cats 0.8 to 1.5 kg. were anesthetized with α-chloralose (80 mg./kg. i.p.). The chest was opened and the heart excised. The heart was dipped and shaken in Tyrode's solution for the removal of blood from the cavities. The right ventricle was then slit open and the small and thin (about 1 mm. in diameter and 4 to 7 mm. in length) papillary muscles were dissected out. A silver wire was attached to each of the two ends of the papillary muscle. The ventricular end was attached to a platinum electrode and mounted in a tissue bath containing Tyrode's solution described above. The silver wire on the valvular end of the muscle was attached to a force displacement transducer for the measurement of the force and rate of muscle contraction. The muscle was stimulated at a rate of 3 beats/sec. by suprathreshold rectangular pulses of 5 millisecond duration. The rest of the procedure was continued as described above.

The in vivo test procedure used is described as follows: Mongrel dogs of both sexes and varying in weight from 9 to 15 kg. were anesthetized with 30 mg./kg. pentobarbital sodium administered intravenously. The trachea was exposed and cannulated. The tracheal cannula was then attached to a Harvard respiratory pump using room air. The right femoral artery and vein were cannulated. The arterial cannula was attached to a Statham P23A pressure transducer connected to a Grass polygraph for the continuous recording of arterial blood pressure. The venous cannula was used for the intravenous administration of drugs. Pin electrodes were attached to the right forelimb and left hindlimb. The electrodes were then connected to a Grass polygraph for the continuous recording of the standard limb lead II electrocardiogram. A ventro-dorsal incision at the third inter-costal space was made, the ribs laterally retracted and the pericardium slit open to expose the myocardium. The base of the aorta was dissected and flow probe was fitted around it. The flow probe was attached to a square wave electromagnetic flowmeter (Carolina Medical Electronics). The flowmeter was then connected to a Grass polygraph for the continuous recording of aortic blood flow. This flow was used as an index of cardiac output (actual cardiac output is aortic blood flow+coronary blood flow). Cardiac contractile force was measured by suturing a Walton-Brodie strain gauge to the wall of the right ventricle. At the end of the surgical procedure, the animal was left to rest and equilibrate for one hour with continuous recording of blood pressure, EKG, cardiac contractile force and aortic blood flow. After the equilibration period, the vehicle or the drug dissolved in the vehicle was administered and the response of all the parameters measured to drug administration was recorded continuously for different periods of times depending on the route of drug administration. The above-described test systems were standardized using ouabain, norepinephrine, Isuprel ® and dopamine.

The compounds of formulas I-VII and XI were subjected to either one of or both the in vitro and in vivo tests. In the in vitro procedure said compounds were effective in producing a 25 to 290% increase in atrial force and a 25 to 350% increase in papillary muscle force at doses ranging from 0.1 F/ml. to 30 F/ml. In the in vivo test the compounds of formulas I-VII and XI effected an increase of from 25 to 260% in cardiac contractile force at doses ranging from 10 F/kg. to 100 mg./kg. administered either intravenously or intraduodenally.

The actual determination of the numerical biological data definitive for a particular compound is readily determined by technicians versed in pharmacological test procedures, without the need for any extensive experimentation.

The compositions of this invention can be administered orally in the form of pills, tablets, capsules, e.g., in admixture with talc, starch, milk sugar or other inert, i.e., non-toxic or pharmacologically acceptable pharmacuetical carrier, or in the form of aqueous solutions, suspensions, encapsulated suspension, gels, elixirs, aqueous alcoholic solutions, e.g., in admixture with sugar or other sweetening agents, flavorings, colorants, thickeners and other conventional pharmaceutical excipients. When injected subcutaneously, intramuscularly or intravenously, usually the latter, they can be administered, e.g., as an aqueous or peanut oil solution or suspension using excipients and carriers conventional for this mode of administration. The best route of administration and the best dosage will be apparent from the laboratory tests for activity and toxicity of the selected compound conventionally undertaken as part of the development phase of a pharmaceutical.

The molecular structures of the compounds of the invention were assigned on the basis of the method of their preparation and study of their NMR spectra, and confirmed by the correspondence between calculated and found values for the elemental analyses of representative examples.

The invention is illustrated by the following examples without, however, being limited thereto.

EXAMPLE 1

A solution containing 6.0 g. of 6,7-dimethoxy-2-naphthaleneethylamine hydrochloride in 150 ml. 48% hydrobromic acid was heated under reflux 1.5 hours. The product, which precipitated upon cooling the reaction mixture, was collected by filtration. Additional product was obtained by evaporation of the filtrate in vacuo. The solids were combined and recrystallized from 20% hydrochloric acid and then from water to yield 3.3 g. of 6-(2-aminoethyl)-2,3-naphthalenediol hydrochloride, m.p. 284°–286° C.

EXAMPLE 2

Following a procedure similar to that described in Example 1 but using 16.0 g. of N-ethyl-6,7-dimethoxy-2-naphthaleneethylamine hydrochloride and 200 ml. of 48% hydrobromic acid afforded 12.0 g. of 6-[2-(ethylamino)ethyl]-2,3-naphthalenediol hydrochloride, m.p. 225°–228° C.

EXAMPLE 3

Following a procedure similar to that described in Example 1 but using 17.0 g. of 1-[2-(6,7-dimethoxy-2-naphthyl)-ethyl]pyrrolidine hydrochloride and 250 ml. of 48% hydrobromic acid provided 11.0 g. of 6-[2-(1-pyrrolidinyl)ethyl]-2,3-naphthalenediol hydrochloride, m.p. 227°–229° C.

EXAMPLE 4

Following a procedure similar to that described in Example 1 but using 6,7-dimethoxy-N,N-dimethyl-2-naphthaleneethylamine hydrochloride afforded 6-[2-(dimethylamino)ethyl]-2,3-naphthalenediol hydrochloride, m.p. 248°–250° C.

EXAMPLE 5

Following a procedure similar to that described in Example 1 but using 14.5 g. of 6,7-dimethoxy-N-methyl-2-naphthaleneethylamine and 200 ml. of 48% HBr afforded 10.0 g. of 6-[2-(methylamino)ethyl]-2,3-naphthalenediol hydrochloride, m.p. 215°–217° C.

EXAMPLE 6

Following a procedure similar to that in Example 1 but using 29.0 g. of N,N-diethyl-6,7-dimethoxy-2-naphthaleneethylamine hydrochloride and 300 ml. of 48% hydrobromic acid afforded 6-[2-(diethylamino)ethyl]-2,3-naphthalenediol hydrochloride, m.p. 195°–197° C. which was dissolved in hot water, cooled, and the aqueous solution made basic with sodium bicarbonate. The resulting free base was collected, washed with water and recrystallized from aqueous ethanol to give 7.7 g. of 6-[2-(diethylamino)ethyl]-2,3-naphthalenediol, m.p. 125°–135° C.

EXAMPLE 7

A solution containing 10.1 g. of 1-[2-(6,7-dimethoxy-2-naphthyl)ethyl]-2-methylpiperidine hydrochloride in 300 ml. of concentrated hydrochloric acid was heated under reflux 2.5 hours, filtered while still hot, and the filtrate cooled overnight at 5°–10° C. The precipitated product was collected and recrystallized from methanol-ether to give 7.0 g. of 6-[2-(2-methyl-1-piperidinyl)ethyl]-2,3-naphthalenediol hydrochloride, m.p. 234°–239° C.

EXAMPLE 8

Following a procedure similar to that in Example 7 but using 10.5 g. of 1-[2-(6,7-dimethoxy-2-naphthyl)ethyl]-piperidine hydrochloride and 400 ml. of concentrated hydrochloric acid afforded 7.0 g. of 6-[2-(1-piperidinyl)ethyl]-2,3-naphthalenediol hydrochloride, m.p. 293°–296° C.

EXAMPLE 9

Following a procedure similar to that in Example 7 but using 4.9 g. of 1-[(6,7-dimethoxy-2-naphthyl)ethyl]-hexamethyleneimine hydrochloride and 140 ml. of concentrated hydrochloric acid yielded 3.8 g. of 6-[2-(1-hexamethyleneiminyl)ethyl]-2,3-naphthalenediol hydrochloride, m.p. 284°–288° C. (dec.).

EXAMPLE 10

Following a procedure similar to that in Example 6 but using 9.7 g. of N-phenyl-6,7-dimethoxy-2-naphthaleneethylamine hydrochloride and 150 ml. of 48% hydrobromic acid, provided 6-(2-anilinoethyl)-2,3-naphthalenediol which was dissolved in ethanol and treated with methanolic hydrogen chloride until acidic. Addition of ether effected precipitation of 2.3 g. of 6-(2-anilinoethyl)-2,3-naphthalenediol hydrochloride, m.p. 215°–218° C.

EXAMPLE 11

Following a procedure similar to that in Example 1 but using 8.8 g. of 6,7-dimethoxy-α-methyl-2-naphthaleneethylamine hydrochloride and 50 ml. of 48% hydrobromic acid, there was obtained 6.3 g. of 6-(2-aminopropyl)-2,3-naphthalenediol hydrochloride, m.p. 242°–245° C.

EXAMPLE 12

Following a procedure similar to that in Example 1 but using 5.3 g. of 6.7-dimethoxy-β,β-dimethyl-2-naphthaleneethylamine hydrochloride and 75 ml. of 48% hydrobromic acid, afforded 4.4 g. of 6-(2-amino-1,1-dimethylethyl)-2,3-naphthalenediol hydrochloride, m.p. >135° C. (dec.).

This compound showed significant antihypertensive activity when administered orally at three dose levels of 12.5, 25 and 50 mg./kg. to adrenal regeneration hypertensive rats prepared according to the methods described by F. R. Shelton, et al., Archives of Internal Medicine 98, 449 (1956) and Circulation Research Supplement 1, Vols. 24 and 25, May 1969 at pages I-35 through 56.

EXAMPLE 13

Following a procedure similar to that in Example 7 but using 5 g. of 6,7-dimethoxy-1-napthaleneethylamine and 200 ml. of concentrated hydrochloric acid yielded 4.8 g. of 5-(2-aminoethyl)-2,3-naphthalenediol hydrochloride, m.p. 95°–105° C.

EXAMPLE 14

Following a procedure similar to that in Example 7 but using 7.0 g. of 6,7-dimethoxy-8-methyl-2-naphthaleneethylamine hydrochloride and 225 ml. of concentrated hydrochloric acid afforded 2.2 g. of 6-(2-aminoethyl)-4-methyl-2,3-naphthalenediol hydrochloride, m.p. 130°–160° C.

EXAMPLE 15

Following a procedure similar to that in Example 6 but using 10.0 g. of 6,7-dimethoxy-2-naphthalenemethylamine and 150 ml. of 48% hydrobromic acid, there was obtained 3.6 g. of 6-(aminomethyl)-2,3-naphthalenediol hydrochloride, m.p. >300° C. (DMF).

EXAMPLE 16

Following a procedure similar to that in Example 7 but using 10.7 g. of N-ethyl-6,7-dimethoxy-2-naphthalenemethylamine hydrochloride and 250 ml. of concentrated hydrochloric acid afforded 5.6 g. of 6-[(ethylamino)methyl]-2,3-naphthalenediol hydrochloride, m.p. 246°–249° C.

EXAMPLE 17

Following a procedure similar to that in Example 7 but using 14.7 g. of N,N-diethyl-6,7-dimethoxy-2-naphthalenemethylamine hydrochloride and 300 ml. of concentrated hydrochloric acid there was obtained 9.2 g. of 6-[(diethylamino)methyl]-2,3-naphthalenediol hydrochloride, m.p. 192°–194° C.

EXAMPLE 18

Following a procedure similar to that in Example 7 but using 10.0 g. of 1-[(6,7-dimethoxy-2-naphthyl)methyl]-pyrrolidine hydrochloride and 300 ml. of concentrated hydrochloric acid provided 6-[(1-pyrrolidinyl)methyl]-2,3-naphthalenediol hydrochloride. Liberation of the free base as in Example 6 afforded 2.6 g. of 6-[(1-pyrrolidinyl)methyl]-2,3-naphthalenediol, m.p. 114°–118° C.

EXAMPLE 19

Following a procedure similar to that in Example 1 but using 2.2 g. of 6,7-dimethoxy-1-naphthalenemethylamine and 50 ml. of 48% hydrobromic acid, there was obtained 1.7 g. of 5-(aminomethyl)-2,3-naphthalenediol hydrochloride, m.p. 246°–248° C.

EXAMPLE 20

Following a procedure similar to that in Example 6 but using 9.0 g. of 2-(tert-butylamino)-6',7'-dimethoxy-2'-acetonaphthone hydrochloride and 100 ml. of 48% hydrobromic acid, yielded 2.5 g. of 2-(tert-butylamino)-6',7'-dihydroxy-2'-acetonaphthone, m.p. >230° C. (dec.) (methanol).

EXAMPLE 21

Following a procedure similar to that in Example 1 but using 11.0 g. of 2-(dimethylamino)-6',7'-dimethoxy-2'-acetonaphthone hydrochloride and 200 ml. of 48% hydrobromic acid, there was obtained 5.6 g. of 2-(dimethylamino)-6',7'-dihydroxy-2'-acetonaphthone hydrochloride, m.p. 246°–250° C.

EXAMPLE 22

Following a procedure similar to that in Example 1 but using 38.5 g. of 2-(benzylmethylamino)-6',7'-dimethoxy-2'-acetonaphthone and 500 ml. of 48% hydrobromic acid yielded 31.0 of 2-(benzylmethylamino)-6',7'-dihydroxy-2'-acetonaphthone hydrochloride, m.p. 229°–231° C.

EXAMPLE 23

Following a procedure similar to that in Example 1 but using 8.5 g. of 2-(tert-butylamino)-6',7'-dimethoxy-1'-acetonaphthone and 250 ml. of 48% hydrobromic acid afforded 7.7 g. of 2-(tert-butylamino)-6',7'-dihydroxy-1'-acetonaphthone hydrochloride, m.p. 248°–250° C. (dec.).

EXAMPLE 24

A solution containing 8.0 g. of 2-(tert-butylamino)-6',7'-dihydroxy-2'-acetonaphthone hydrochloride and 100 mg. of 10% palladium-on-carbon in 100 ml. of dimethylformamide was shaken under a hydrogen pressure of 20–50 psi for approximately six hours or until one molar equivalent of hydrogen was absorbed. The catalyst was removed by filtration and the filtrate was evaporated in vacuo. The residue was dissolved in water and the aqueous solution made basic with sodium bicarbonate. The resulting precipitate was collected and recrystallized from dimethylformamide-ethanol to give 3.8 g. of α-[(tert-butylamino)-methyl]-6,7-dihydroxy-2-naphthalenemethanol, m.p. >300° C.

EXAMPLE 25

Following a procedure similar to that in Example 24 but using 7.8 g. of 2-(tert-butylamino)-6',7'-didhydroxy-1'-acetonaphthone, there was obtained 1.4 g. of α-[(tert-butylamino)methyl]-6,7-dihydroxy-1-naphthalenemethanol hydrate, m.p. 140°–144° C.

EXAMPLE 26

A solution containing 30.0 g. of 2-(benzylmethylamino)-6',7'-dihydroxy-2'-acetonaphthone and 300 mg. of 10% palladium on carbon in 300 ml. of dimethylformamide was shaken under a hydrogen pressure of 20–50 psi until one molar equivalent of hydrogen was absorbed. The reaction mixture was then warmed to 50° C. and after approximately six hours a second molar equivalent of hydrogen was absorbed. The catalyst was removed by filtration and the filtrate was evaporated in vacuo. The residue was dissolved in water and the aqueous solution made basic with sodium bicarbonate. The resulting precipitate was collected and recrystallized from dimethylformamide to give 10.0 g. of 6,7-dihydroxy-α-[(methylamino)methyl]-2-naphthalenemethanol, m.p. >300° C.

EXAMPLE 27

A solution containing 6.8 g. of diethyl 2-acetamido-2-(6,7-dimethoxy-2-naphthylmethyl)malonate in 100 ml. of acetic acid was heated under reflux while concentrated hydrochloric acid was added dropwise at a rate sufficient to maintain a homogeneous solution. After three hours, 250 ml. of acid had been added. The mixture was heated under reflux an additional two hours, then cooled, diluted with 200 ml. of water and filtered to remove impurities. Evaporation of the filtrate in vacuo followed by trituration of the residue in acetonitrile for three hours afforded 3.0 g. of (6,7-dihydroxy-2-naphthyl)alanine hydrochloride, m.p. 242°–246° C. (dec.).

EXAMPLE 28

A suspension of 3.8 g. of 6,8-dimethoxy-1-naphthaleneethylamine hydrochloride in 6 N hydrochloric acid under nitrogen was heated to the reflux temperature over a period of 0.5 hours. Reflux was maintained five minutes and the reaction allowed to cool. The process was repeated and the cooled mixture was then evaporated to dryness. The residue was dissolved in ethanol and diluted with ether to give 3.0 g. of 8-(2-aminoethyl)-1,3-naphthalenediol hydrochloride, m.p. 95°–105° C.

EXAMPLE 29

Following a procedure similar to that in Example 7 but using 6.0 g. of N,N-diethyl-4,8-dimethoxy-1-naphthaleneethylamine hydrochloride and 100 ml. of concentrated hydrochloric acid, there was obtained 2.7 g. of 4-[2-(diethylamino)ethyl]-1,5-naphthalenediol hydrochloride, m.p. 235°–237° C. (dec.).

EXAMPLE 30

Following a procedure similar to that in Example 7 but using 9.6 g. of 1-[2-(4,8-dimethoxy-1-naphthyl)ethyl]-pyrrolidine hydrochloride and 250 ml. of concentrated hydrochloric acid, yielded 3.1 g. of 4-[2-(1-pyrrolidinyl)ethyl]-1,5-naphthalenediol hydrochloride, m.p. 216°–218° C. (dec.).

EXAMPLE 31

A solution containing 5.0 g. of 6-methoxy-2-naphthaleneethylamine hydrochloride in 50 ml. of 48% hydrobromic acid was heated on the steam bath two hours followed by heating one hour under reflux. The reaction mixture was evaporated to dryness in vacuo and the residue recrystallized from methanol-ether to give 3.8 g. of 6-(2-aminoethyl)-2-naphthol hydrobromide, m.p. 289°–291° C.

EXAMPLE 32

Following a procedure similar to that in Example 31 but using 8.5 g. of N-ethyl-6-methoxy-2-naphthaleneethylamine hydrochloride and 64 ml. of 48% hydrobromic acid, there was obtained 6.7 g. of 6-[2-(ethylamino)ethyl]-2-naphthol hydrobromide, m.p. 227°–228° C.

EXAMPLE 33

Following a procedure similar to that in Example 31 but using 7.0 g. of 1-[2-(6-methoxy-2-naphthyl)ethyl]-pyrrolidine hydrochloride and 28 ml. of 48% hydrobromic acid, yielded 6.5 g. of 6-[2-(1-pyrrolidinyl)ethyl]-2-naphthol hydrobromide, m.p. 207°–208.5° C.

EXAMPLE 34

Following a procedure similar to that in Example 31 but using 5.0 g. of 6-methoxy-β-methyl-2-naphthaleneethylamine hydrochloride and 35 ml. of 48% hydrobromic acid, afforded 4.9 g. of 6-(2-amino-1-methylethyl)-2-naphthol hydrobromide, m.p. 236°–236.5° C.

EXAMPLE 35

Following a procedure similar to that described in Example 31 but using 7.0 g. of 1-[2-(6-methoxy-2-naphthyl)propyl]pyrrolidine hydrochloride and 30 ml. of 48% hydrobromic acid, there was obtained 2.1 g. of 6-[1-methyl-2-(1-pyrrolidinyl)-ethyl]-2-naphthol hydrobromide, m.p. 189°-191° C.

EXAMPLE 36

A 1.1-gram sample of 7-methoxy-2-naphthaleneethylamine hydrochloride was added portionwise to 20 ml. of refluxing 48% hydrobromic acid. When addition was complete the mixture was heated under reflux for one hour. Upon cooling the product precipitated. The product was collected, combined with another batch prepared from 3.1 g. of 7-methoxy-2-naphthaleneethylamine hydrochloride and recrystallized from methanol-ether to give 2.7 g. of 7-(2-aminoethyl)-2-naphthol hydrobromide, m.p. 237°-237.5° C.

EXAMPLE 37

Following a procedure similar to that in Example 36 but using 5.0 g. of N-(1-methyl-3-phenylpropyl)-6,7-dimethoxy-2-naphthaleneethylamine hydrochloride and 40 ml. of 48% hydrobromic acid, there was obtained 4.1 g. of 6-{2-[(1-methyl-3-phenylpropyl)amino]ethyl}-2,3-naphthalenediol hydrobromide, m.p. 182° C.

EXAMPLE 38

Following a procedure similar to that in Example 31 but using 7.0 g. of N-[3-(p-methoxyphenyl)-1-methylpropyl]-6,7-dimethoxy-2-naphthaleneethylamine hydrochloride and 105 ml. of 48% hydrobromic acid provided 5.4 g. of 6-<2-{[3-(p-hydroxyphenyl)-1-methylpropyl]amino}ethyl>-2,3-naphthalenediol hydrobromide, m.p. 232°-232.5° C.

EXAMPLE 39

To a stirred solution containing 5.0 g. of 6-(2-aminoethyl)-2,3-naphthalenediol hydrochloride in 70 ml. of trifluoroacetic acid at 0° C. was added dropwise 8.0 g. of acetyl chloride. When the addition was complete the mixture was stirred at 0° C. three hours and then at room temperature one hour. The reaction mixture was then diluted with 80 ml. of water and stirred an additional hour at room temperature. Following evaporation of the reaction mixture in vacuo the residue was allowed to crystallize slowly overnight. Recrystallization from 2-propanol afforded 3.0 g. of 6-(2-aminoethyl)-2,3-naphthalenediol diacetate hydrochloride, m.p. 181°-183° C.

By following a procedure similar to that described in Example 39 but substituting for 6-(2-aminoethyl)-2,3-naphthalenediol hydrochloride an equivalent amount of the following:

6-[2-(methylamino)ethyl]-2,3-naphthalenediol hydrochloride;
6-[2-(ethylamino)ethyl]-2,3-naphthalenediol hydrochloride;
6-[2-(dimethylamino)ethyl]-2,3-naphthalenediol hydrochloride;
6-[2-(diethylamino)ethyl]-2,3-naphthalenediol hydrochloride;
6-(2-anilinoethyl)-2,3-naphthalenediol hydrochloride;
6-[2-(1-pyrrolidinyl)ethyl]-2,3-naphthalenediol hydrochloride;
6-(2-aminoethyl)-4-methyl-2,3-naphthalenediol hydrochloride;
5-(2-aminoethyl)-2,3-naphthalenediol hydrochloride;
5-(2-aminoethyl)-4-methyl-2,3-naphthalenediol hydrochloride;
5-(2-aminopropyl)-2,3-naphthalenediol hydrochloride;
6-(2-amino-1,1-dimethylethyl)-2,3-naphthalenediol hydrochloride;
6-[2-(ethylamino)-1,1-dimethylethyl]-2,3-naphthalenediol hydrochloride;
6-(2-amino-1,1-dimethylethyl)-4-methyl-2,3-naphthalenediol hydrochloride;
5-(2-amino-1,1-dimethylethyl)-2,3-naphthalenediol hydrochloride;
6-(aminomethyl)-2,3-naphthalenediol hydrochloride;
6-[(benzylamino)methyl]-2,3-naphthalenediol hydrochloride;
2-(dimethylamino)-6',7'-dihydroxy-2'-acetonaphthone hydrochloride;
2-(benzylmethylamino)-6',7'-dihydroxy-2'-acetonaphthone hydrochloride;
6',7'-dihydroxy-2-(1-pyrrolidinyl)-1'-acetonaphthone hydrochloride;
6',7'-dihydroxy-8'-methyl-2-(1-pyrrolidinyl)-2'-propionaphthone hydrochloride;
(6,7-dihydroxy-2-naphthyl)alanine hydrochloride;
8-(2-aminoethyl)-1,3-naphthalenediol hydrochloride;
8-{2-[4-(2,6-dimethylmorpholinyl)]ethyl}-1,3-naphthalenediol hydrochloride;
7-(2-aminoethyl)-1,3-naphthalenediol hydrochloride;
5-(2-aminoethyl)-1,2-naphthalenediol hydrochloride;
6-(2-aminoethyl)-1,2-naphthalenediol hydrochloride;
4-[2-diethylamino)ethyl]-1,5-naphthalenediol hydrochloride, and
4-(2-aminopropyl)-1,5-naphthalenediol hydrochloride; there are obtained respectively:
6-[2-(methylamino)ethyl]-2,3-naphthalenediol diacetate hydrochloride;
6-[2-(ethylamino)ethyl]-2,3-naphthalenediol diacetate hydrochloride;
6-[2-(dimethylamino)ethyl]-2,3-naphthalenediol diacetate hydrochloride;
6-[2-(diethylamino)ethyl]-2,3-naphthalenediol diacetate hydrochloride;
6-(2-anilinoethyl)-2,3-naphthalenediol diacetate hydrochloride;
6-[2-(1-pyrrolidinyl)ethyl]-2,3-naphthalenediol diacetate hydrochloride;
6-(2-aminoethyl)-4-methyl-2,3-naphthalenediol diacetate hydrochloride;
5-(2-aminoethyl)-2,3-naphthalenediol diacetate hydrochloride;
5-(2-aminoethyl)-4-methyl-2,3-naphthalenediol diacetate hydrochloride;
5-(2-aminopropyl)-2,3-naphthalenediol diacetate hydrochloride;
6-(2-amino-1,1-dimethylethyl)-2,3-naphthalenediol diacetate hydrochloride;
6-[2-(ethylamino)-1,1-dimethylethyl]-2,3-naphthalenediol diacetate hydrochloride;
6-(2-amino-1,1-dimethylethyl)-4-methyl-2,3-naphthalenediol diacetate hydrochloride;
5-(2-amino-1,1-dimethylethyl)-2,3-naphthalenediol diacetate hydrochloride;
6-(aminomethyl)-2,3-naphthalenediol diacetate hydrochloride;
6-[(benzylamino)methyl]-2,3-naphthalenediol diacetate hydrochloride;
6',7'-diacetoxy-2-(dimethylamino)-2'-acetonaphthone hydrochloride;
6',7'-diacetoxy-2-(benzylmethylamino)-2'-acetonaphthone hydrochloride;

6',7'-diacetoxy-2-(1-pyrrolidinyl)-1'-acetonaphthone hydrochloride; 6',7'-diacetoxy-8'-methyl-2-(1-pyrrolidinyl)-2'-propionaphthone hydrochloride;

(6,7-diacetoxy-2-naphthyl)alanine hydrochloride;

8-(2-aminoethyl)-1,3-naphthalenediol diacetate hydrochloride;

8-{2-[4-(2,6-dimethylmorpholinyl)]ethyl}-1,3-naphthalenediol diacetate hydrochloride;

7-(2-aminoethyl)-1,3-naphthalenediol diacetate hydrochloride;

5-(2-aminoethyl)-1,2-naphthalenediol diacetate hydrochloride;

6-(2-aminoethyl)-1,2-naphthalenediol diacetate hydrochloride;

4-[2-(diethylamino)ethyl]-1,5-naphthalenediol diacetate hydrochloride, and 4-(2-aminopropyl)-1,5-naphthalenediol diacetate hydrochloride.

By following a procedure similar to that described in Example 39 but substituting for acetyl chloride an equivalent amount of acetyl bromide and for 6-(2-aminoethyl)-2,3-naphthalenediol hydrochloride an equivalent amount of the following:

6-(2-aminoethyl)-2-naphthol hydrobromide;

6-[2-(benzylamino)ethyl]-2-naphthol hydrobromide;

6-(2-aminopropyl)-2-naphthol hydrobromide;

6-(2-amino-1-methylethyl)-2-naphthol hydrobromide, and 6-{2-[(1-methyl-3-phenylpropyl)amino]ethyl}-2,3-naphthalenediol hydrobromide;

there are obtained respectively:

6-(2-aminoethyl)-2-naphthol acetate hydrobromide;

6-[2-(benzylamino)ethyl]-2-naphthol acetate hydrobromide;

6-(2-aminopropyl)-2-naphthol acetate hydrobromide;

6-(2-amino-1-methylethyl)-2-naphthol acetate hydrobromide, and

6-{2-[(1-methyl-3-phenylpropyl)amino]ethyl}-2,3-naphthalenediol diacetate hydrobromide.

By following a procedure similar to that described in Example 39 but substituting for acetyl chloride an equivalent amount of propionyl chloride, and for 6-(2-aminoethyl)-2,3-naphthalenediol hydrochloride an equivalent amount of the following:

6-[2-(1-piperidinyl)ethyl]-2,3-naphthalenediol hydrochloride;

6-[2-(2-methyl-1-piperidinyl)ethyl]-2,3-naphthalenediol hydrochloride;

6-[2-(1-hexamethyleneiminyl)ethyl]-2,3-naphthalenediol hydrochloride;

6-[2-(isopropylamino)ethyl]-2,3-naphthalenediol hydrochloride;

6-[2-(ethylamino)propyl]-4-methyl-2,3-naphthalenediol hydrochloride;

5-[2-(1-pyrrolidinyl)propyl]-4-methyl-2,3-naphthalenediol hydrochloride;

5-[2-(ethylamino)-1,1-dimethylethyl]-2,3-naphthalenediol hydrochloride;

6-[(ethylamino)methyl]-2,3-naphthalenediol hydrochloride;

6-aminomethyl-4-methyl-2,3-naphthalenediol hydrochloride;

2-amino-6',7'-dihydroxy-2'-acetonaphthone hydrochloride;

2-(tert-butylamino)-6',7'-dihydroxy-1'-acetonaphthone hydrochloride;

(6,7-dihydroxyl-1-naphthyl)alanine hydrochloride;

8-[2-(ethylamino)ethyl]-1,3-naphthalenediol hydrochloride;

8-(2-amino-1,1-dimethylethyl9-1,3-naphthalenediol hydrochloride;

6-[2-(ethylamino)ethyl]-1,2-naphthalenediol hydrochloride, and

4-[2-(1-pyrrolidinyl)ethyl]-1,5-naphthalenediol hydrochloride; there are obtained respectively:

6-[2-(1-piperidinyl)ethyl]-2,3-naphthalenediol dipropionate hydrochloride;

6-[2-(2-methyl-1-piperidinyl)ethyl]-2,3-naphthalenediol dipropionate hydrochloride;

6-[2-(1-hexamethyleneiminyl)ethyl]-2,3-naphthalenediol dipropionate hydrochloride;

6-[2-(isopropylamino)ethyl]-2,3-naphthalenediol dipropionate hydrochloride;

6-[3-(ethylamino)propyl]-4-methyl-2,3-naphthalenediol hydrochloride;

5-[2-(1-pyrrolidinyl)propyl]-4-methyl-2,3-naphthalenediol dipropionate hydrochloride;

5-[2-(ethylamino)-1,1-dimethylethyl]-2,3-naphthalenediol dipropionate hydrochloride;

6-[(ethylamino)methyl]-2,3-naphthalenediol dipropionate hydrochloride;

6-aminomethyl-4-methyl-2,3-naphthalenediol dipropionate hydrochloride;

2-amino-6',7'-dipropionyloxy-2'-acetonaphthone hydrochloride;

2-(tert-butylamino)-6',7'-dipropionyloxy-1'-acetonaphthone hydrochloride;

(6,7-dipropionyloxy-1-naphthyl)alanine hydrochloride;

8-[2-(ethylamino)ethyl]-1,3-naphthalenediol dipropionate hydrochloride;

8-(2-amino-1,1-dimethylethyl)-1,3-naphthalenediol dipropionate hydrochloride;

6-[2-(ethylamino)ethyl]-1,2-naphthalenediol dipropionate hydrochloride, and

4-[2-(1-pyrrolidinyl)ethyl]-1,5-naphthalenediol dipropionate hydrochloride.

By following a procedure similar to that described in Example 39 but substituting for acetyl chloride an equivalent amount of propionyl bromide, and for 6-(2-aminoethyl)-2,3-naphthalenediol hydrochloride an equivalent amount of the following:

6-[2-(methylamino)ethyl]-2-naphthol hydrobromide;

6-(2-anilinoethyl)-2-naphthol hydrobromide;

7-(2-amino-1-methylethyl)-2-naphthol hydrobromide, and

6-{[2-(1-methyl-3-phenylpropyl)amino]ethyl}-2-naphthol hydrobromide;

there are obtained respectively:

6-[2-(methylamino)ethyl]-2-naphthol propionate hydrobromide;

6-(2-anilinoethyl)-2-naphthol propionate hydrobromide;

7-(2-amino-1-methylethyl)-2-naphthol propionate hydrobromide, and

6-{[2(1-methyl-3-phenylpropyl)amino]ethyl}-2-naphthol propionate hydrobromide.

EXAMPLE 40

To a stirred suspension of 4.0 g. of 6-(2-aminoethyl)-2,3-naphthalenediol hydrochloride in 50 ml. of trifluoroacetic acid at 0° C. was added dropwise 10.5 g. of p-toluyl chloride. When the addition was complete the mixture was stirred one hour at 0° C. and then two hours at room temperature. The reaction mixture was then diluted with 50 ml. of water and stirred an additional two hours at room temperature. Following evaporation of the reaction mixture in vacuo, the residue was partitioned between ethyl acetate and saturated aqueous sodium bicarbonate. After separating the layers, the aqueous portion was re-extracted with ethyl acetate. The combined organic extracts were washed with water, dried over anhydrous magnesium sulfate and evaporated in vacuo. The residue was dissolved in methanol and treated with methanolic hydrogen chloride until acidic. Addition of ether and cooling precipitated the salt. Two recrystallizations from ethanol-ether afforded 2.2 g. of 6-(2-aminoethyl)-2,3-naphthalenediol di-p-toluate hydrochloride, m.p. 188°–190° C.

By following a procedure similar to that described in Example 40 but substituting for 6-(2-aminoethyl)-2,3-naphthalenediol hydrochloride an equivalent amount of the following:

6-[2-(1-pyrrolidinyl)ethyl]-2,3-naphthalenediol hydrochloride;
6-[2-(4-morpholinyl)ethyl]-2,3-naphthalenediol hydrochloride;
6-[2-(benzylamino)ethyl]-2,3-naphthalenediol hydrochloride;
6-{2-[4-(2,6-dimethylmorpholinyl)]ethyl}-2,3-naphthalenediol hydrochloride;
6-(2-aminopropyl)-2,3-naphthalenediol hydrochloride;
6-(2-amino-1,1-dimethylethyl)-2,3-naphthalenediol hydrochloride;
5-(aminomethyl)-2,3-naphthalenediol hydrochloride;
2-(ethylamino)-6',7'-dihydroxy-8'-methyl-1'-acetonaphthone hydrochloride;
2-amino-6',7'-dihydroxy-1'-propionaphthone hydrochloride;
6',7'-dihydroxy-8'-methyl-2-(1-pyrrolidinyl)-1'-propionaphthone hydrochloride;
(6,7-dihydroxy-1-naphthyl)alanine hydrochloride;
8-[2-(1-piperidinyl)ethyl]-1,3-naphthalenediol hydrochloride;
5-[2-(1-hexamethyleneiminyl)ethyl]-1,2-naphthalenediol hydrochloride;
6-[2-(1-pyrrolidinyl)-1,1-dimethylethyl]-1,2-naphthalenediol hydrochloride;
4-(2-anilinoethyl)-1,5-naphthalenediol hydrochloride, and
4-[2-(1-pyrrolidinyl)propyl]-1,5-naphthalenediol hydrochloride; there are obtained respectively:
6-[2-(1-pyrrolidinyl)ethyl]-2,3-naphthalenediol di-p-toluate hydrochloride;
6-[2-(4-morpholinyl)ethyl]-2,3-naphthalenediol di-p-toluate hydrochloride;
6-[2-(benzylamino)ethyl]-2,3-naphthalenediol di-p-toluate hydrochloride;
6-{2-[4-(2,6-dimethylmorpholinyl)]ethyl}-2,3-naphthalenediol di-p-toluate hydrochloride;
6-(2-aminopropyl)-2,3-naphthalenediol di-p-toluate hydrochloride;
6-(2-amino-1,1-dimethylethyl)-2,3-naphthalenediol di-p-toluate hydrochloride;
5-(aminomethyl)-2,3-naphthalenediol di-p-toluate hydrochloride;
2-(ethylamino)-8'-methyl-6',7'-di-p-toluyloxy-1'-acetonaphthone hydrochloride;
2-amino-6',7'-di-p-toluyloxy-1'-propionaphthone hydrochloride;
8'-methyl-2-(1-pyrrolidinyl)-6',7'-di-p-toluyloxy-1'-propionaphthone hydrochloride;
(6,7-di-p-toluyloxy-1-naphthyl)alanine hydrochloride;
8-[2-(1-piperidinyl)ethyl]-1,3-naphthalenediol di-p-toluate hydrochloride;
5-[2-(1-hexamethyleneiminyl)ethyl]-1,2-naphthalenediol di-p-toluate hydrochloride;
6-[2-(1-pyrrolidinyl)-1,1-dimethylethyl]-1,2-naphthalenediol di-p-toluate hydrochloride;
4-(2-anilinoethyl)-1,5-naphthalenediol di-p-toluate hydrochloride, and
4-[2-(1-pyrrolidinyl)propyl]-1,5-naphthalenediol di-p-toluate hydrochloride.

By following a procedure similar to that described in Example 40 but substituting for p-toluyl chloride an equivalent amount of p-toluyl bromide and for 6-(2-aminoethyl)2,3-naphthalenediol hydrochloride an equivalent amount of the following:

6-[2-(1-pyrrolidinyl)ethyl]-2-naphthol hydrobromide;
6-[2-(n-butylamino)ethyl]-2-naphthol hydrobromide;
7-(2-aminoethyl)-2-naphthol hydrobromide;
7-(2-amino-1,1-dimethylethyl)-2-naphthol hydrobromide, and
6-<2-{[3-(p-methoxyphenyl)-1-methylpropyl]amino}ethyl>-2,3-naphthalenediol hydrobromide;
there are obtained respectively:
6-[2-(1-pyrrolidinyl)ethyl]-2-naphthol p-toluate hydrobromide;
6-[2-(n-butylamino)ethyl]-2-naphthol p-toluate hydrobromide;
7-(2-aminoethyl)-2-naphthol p-toluate hydrobromide;
7-(2-amino-1,1-dimethylethyl)-2-naphthol p-toluate hydrobromide, and
6-<2-{[3-(p-methoxyphenyl)-1-methylpropyl]amino}ethyl>-2,3-naphthalenediol di-p-toluate hydrobromide.

By following a procedure similar to that described in Example 40 but substituting for p-toluyl chloride an equivalent amount of benzoyl chloride and for 6-(2-aminoethyl)-2,3-naphthalenediol hydrochloride an equivalent amount of the following:

6-[2-(ethylamino)ethyl]-4-methyl-2,3-naphthalenediol hydrochloride;
6-[2-(1-pyrrolidinyl)ethyl]-4-methyl-2,3-naphthalenediol hydrochloride;
5-[2-(1-pyrrolidinyl)-1-methylethyl]-2,3-naphthalenediol hydrochloride;
6-[(tert-butylamino)methyl]-2,3-naphthalenediol hydrochloride;
6',7'-dihydroxy-8'-methyl-2-(1-pyrrolidinyl)-2'-acetonaphthone hydrochloride;
8-[2-(1-pyrrolidinyl)ethyl]-1,3-naphthalenediol hydrochloride;
7-(2-amino-1-methylethyl)-1,3-naphthalenediol hydrochloride;
5-(2-amino-1,1-dimethylethyl)-1,2-naphthalenediol hydrochloride, and
4-[2-(1-piperidinyl)ethyl]-1,5-naphthalenediol hydrochloride; there are obtained respectively:
6-[2-(ethylamino)ethyl]-4-methyl-2,3-naphthalenediol dibenzoate hydrochloride;
6-[2-(1-pyrrolidinyl)ethyl]-4-methyl-2,3-naphthalenediol dibenzoate hydrochloride;
5-[2-(1-pyrrolidinyl)-1-methylethyl]-2,3-naphthalenediol dibenzoate hydrochloride;
6-[(tert-butylamino)methyl]-2,3-naphthalenediol dibenzoate hydrochloride;
6',7'-dibenzoyloxy-8'-methyl-2-(1-pyrrolidinyl)-2'-acetonaphthone hydrochloride;
8-[2-(1-pyrrolidinyl)ethyl]-1,3-naphthalenediol dibenzoate hydrochloride;

7-(2-amino-1-methylethyl)-1,3-naphthalenediol dibenzoate hydrochloride;

5-(2-amino-1,1-dimethylethyl)-1,2-naphthalenediol dibenzoate hydrochloride, and

4-[2-(1-piperidinyl)ethyl]-1,5-naphthalenediol hydrochloride.

By following a procedure similar to that described in Example 40 but substituting for p-toluyl chloride an equivalent amount of benzoyl bromide, and for 6-(2-aminoethyl)2,3-naphthalenediol hydrochloride an equivalent amount of the following.

6-[2-(isopropylamino)ethyl]-2-naphthol hydrobromide;

6-[2-(1-pyrrolidinyl)-1,1-dimethylethyl]-2-naphthol hydrobromide, and

7-{2-[(1-methyl-3-phenylpropyl)amino]ethyl}-2-naphthol hydrobromide;

there are obtained respectively:

6-[2-(isopropylamino)ethyl]-2-naphthol benzoate hydrobromide;

6-[2-(1-pyrrolidinyl)-1,1-dimethylethyl]-2-naphthol benzoate hydrobromide, and

7-{2-[(1-methyl-3-phenylpropyl)amino]ethyl}-2-naphthol benzoate hydrobromide.

EXAMPLE 41

A solution containing 6.0 g. of 6-(2-aminoethyl)-2,3-naphthalenediol hydrochloride and 16 g. of isobutyryl chloride in 75 ml. of trifluoroacetic acid was heated under reflux overnight. The cooled reaction mixture was diluted with 200 ml. of water and stirred at room temperature two hours. Following evaporation of the solvents in vacuo the residue was triturated with chloroform and a chloroform-insoluble material was removed by filtration. Addition of ether to the filtrate precipitated the desired product which was recrystallized from chloroform-n-hexane to give 2.6 g. of 6-(2-aminoethyl)-2,3-naphthalenediol diisobutyrate hydrochloride, m.p. 135°–138° C.

By following a procedure similar to that described in Example 41 but substituting for 6-(2-aminoethyl)-2,3-naphthalenediol hydrochloride an equivalent amount of the following:

6-[2-(ethylamino)ethyl]-2,3-naphthalenediol hydrochloride;

6-[2-(1-pyrrolidinyl)ethyl]-2,3-naphthalenediol hydrochloride;

6-[2-(tert-butylamino)ethyl]-2,3-naphthalenediol hydrochloride;

6-[2-(ethylmethylamino)ethyl]-2,3-naphthalenediol hydrochloride;

6-[2-(n-butylamino)ethyl]-2,3-naphthalenediol hydrochloride;

4-methyl-6-[2-(1-pyrrolidinyl)ethyl]-2,3-naphthalenediol hydrochloride;

6-(2-amino-1,1-dimethylethyl)-2,3-naphthalenediol hydrochloride;

5-(2-amino-1-methylethyl)-4-methyl-2,3-naphthalenediol hydrochloride;

6-[(diethylamino)methyl]-2,3-naphthalenediol hydrochloride;

6-(2-methylpiperidinyl)methyl-2,3-naphthalenediol hydrochloride;

5-(ethylaminomethyl)-4-methyl-2,3-naphthalenediol hydrochloride;

2-(tert-butylamino)-6',7'-dihydroxy-2'-acetonaphthone hydrochloride;

6',7'-dihydroxy-2-(1-pyrrolidinyl)-2'-acetonaphthone hydrochloride;

2-anilino-6',7'-dihydroxy-2'-acetonaphthone hydrochloride;

2-amino-6',7'-dihydroxy-1'-propionaphthone hydrochloride;

(6,7-dihydroxy-2-naphthyl)alanine hydrochloride;

5-[2-(isopropylamino)ethyl]-1,2-naphthalenediol hydrochloride, and 5-(2-aminoethyl)-1,5-naphthalenediol hydrochloride; there are obtained respectively:

6-[2-(ethylamino)ethyl]-2,3-naphthalenediol diisobutyrate hydrochloride;

6-[2-(1-pyrrolidinyl)ethyl]-2,3-naphthalenediol diisobutyrate hydrochloride;

6-[2-(tert-butylamino)ethyl]-2,3-naphthalenediol diisobutyrate hydrochloride;

6-[2-(ethylmethylamino)ethyl]-2,3-naphthalenediol diisobutyrate hydrochloride;

6-[2-(n-butylamino)ethyl]-2,3-naphthalenediol diisobutyrate hydrochloride;

4-methyl-6-[2-(1-pyrrolidinyl)ethyl]-2,3-naphthalenediol diisobutyrate hydrochloride;

6-(2-amino-1,1-dimethylethyl)-2,3-naphthalenediol diisobutyrate hydrochloride;

5-(2-amino-1-methylethyl)-4-methyl-2,3-naphthalenediol diisobutyrate hydrochloride;

6-[(diethylamino)methyl]-2,3-naphthalenediol diisobutyrate hydrochloride;

6-(2-methylpiperidinyl)methyl-2,3-naphthalenediol diisobutyrate hydrochloride;

5-[(ethylamino)methyl]-4-methyl-2,3-naphthalenediol diisobutyrate hydrochloride;

2-(tert-butylamino)-6',7'-diisobutyryloxy-2'-acetonaphthone hydrochloride;

6',7'-diisobutyryloxy-2-(1-pyrrolidinyl)-2'-acetonaphthone hydrochloride;

2-anilino-6',7'-diisobutyryloxy-2'-acetonaphthone hydrochloride;

2-amino-6',7'-diisobutyryloxy-1'-propionaphthone hydrochloride;

(6,7-diisobutyryloxy-2-naphthyl)alanine hydrochloride;

5-[2-(isopropylamino)ethyl]-1,2-naphthalenediol diisobutyrate hydrochloride, and 5-(2-aminoethyl)-1,5-naphthalenediol diisobutyrate hydrochloride.

By following a procedure similar to that described in Example 41 but substituting for isobutyryl chloride an equivalent amount of isobutyryl bromide, and for 6-(2-aminoethyl)2,3-naphthalenediol hydrochloride an equivalent amount of the following:

6-[2-(ethylamino)ethyl]-2-naphthol hydrobromide;

6-[2-(1-hexamethyleneiminyl)ethyl]-2-naphthol hydrobromide;

6-[2-(1-pyrrolidinyl)-1-methylethyl]-2-naphthol hydrobromide;

7-[2-(1-pyrrolidinyl)propyl]-2-naphthol hydrobromide, and

6-<2-{[3-(p-hydroxyphenyl)-1-methylpropyl]amino}ethyl>-2,3-naphthalenediol hydrobromide;

there are obtained respectively:

6-[2-(ethylamino)ethyl]-2-naphthol isobutyrate hydrobromide;

6-[2-(1-hexamethyleneiminyl)ethyl]-2-naphthol isobutyrate hydrobromide;

6-[2-(1-pyrrolidinyl)-1-methylethyl]-2-naphthol isobutyrate hydrobromide;

7-[2-(1-pyrrolidinyl)propyl]-2-naphthol isobutyrate hydrobromide, and

6-<2-{[3-(p-isobutyryloxyphenyl)-1-methylpropyl]amino}ethyl>-2,3-naphthalenediol diisobutyrate hydrobromide.

EXAMPLE 42

To a stirred mixture of 6.0 g. of 6-(2-aminoethyl)-2,3-naphthalenediol hydrochloride and 75 ml. of trifluoroacetic acid at 0° C. was added dropwise 11.0 g. of isobutyryl chloride. When the addition was complete the mixture was stirred three hours at 0° C. and then at room temperature overnight. The reaction was then diluted with 150 ml. of water and stirred an additional two hours. The resulting oily salt was drawn off, dissolved in methanolic hydrogen chloride and precipitated with ether. Remaining traces of water were driven off by dissolving the product in methanol adding benzene and evaporating to dryness in vacuo. Recrystallization from 2-propanol-ether afforded 5.5 g. of 6-(2-aminoethyl)-2,3-naphthalenediol 3(or 2)isobutyrate hydrochloride, m.p. 250°-260° C. (with sintering at 200° C.)

By following a procedure similar to that described in Example 42 but substituting for 6-(2-aminoethyl)-2,3-naphthalenediol hydrochloride an equivalent amount of the following:

6-[2-(ethylamino)ethyl]-2,3-naphthalenediol hydrochloride;

6-[(1-pyrrolidinyl)methyl]-2,3-naphthalenediol hydrochloride;

2-(ethylamino)-6',7'-dihydroxy-2'-acetonaphthone hydrochloride;

8-[2-(diethylamino)ethyl]-1,3-naphthalenediol hydrochloride;

5-[2-(1-pyrrolidinyl)ethyl]-1,2-naphthalenediol hydrochloride; and

4-[2-(ethylamino)ethyl]-1,5-naphthalenediol hydrochloride; there are obtained respectively:

6-[2-(ethylamino)ethyl]-2,3-naphthalenediol 2(or 3)-isobutyrate hydrochloride;

6-[(1-pyrrolidinyl)methyl]-2,3-naphthalenediol 2(or 3)-isobutyrate hydrochloride;

2-(ethylamino)-6'(or 7')-hydroxy-7'(or 6')-isobutyryloxy-2'-acetonaphthone hydrochloride;

8-[2-(diethylamino)ethyl]-1,3-naphthalenediol 3(or 1)isobutyrate hydrochloride;

5-[2-(1-pyrrolidinyl)ethyl]-1,2-naphthalenediol 1(or 2)isobutyrate hydrochloride; and 4-[2-(ethylamino)ethyl]-1,5-naphthalenediol 1(or 5)isobutyrate hydrochloride.

EXAMPLE 43

A mixture containing 7.0 g. of 6',7'-dimethoxy-2-(dimethylamino)-2'-acetonaphthone hydrochloride, 80 ml. of acetic acid, 10 ml. of water, 10 ml. of concentrated hydrochloric acid, and 1.0 g. of 10% palladium-on-carbon was shaken under a hydrogen pressure of 10-50 psi at 40°-50° C. until two equivalents of hydrogen were absorbed (approximately seven hours). The catalyst was removed by filtration and the filtrate was evaporated to dryness in vacuo. The residue was partitioned between chloroform and dilute aqueous sodium hydroxide. The chloroform extracts were dried over anhydrous sodium sulfate and evaporated to dryness in vacuo. The residue was dissolved in 2-propanol and treated with methanolic hydrogen chloride until acidic. Evaporation to dryness in vacuo left a solid which was recrystallized twice from methanol-ether to give 4.5 g. of 6,7-dimethoxy-N,N-dimethyl-2-naphthaleneethylamine hydrochloride, m.p. 222°-223° C. (dec.).

EXAMPLE 44

Following a procedure similar to that in Example 43 but using 7.2 g. of 2-(tert-butylamino)-6'7'-dimethoxy-2'-acetonaphthone, there was obtained 3.9 g. of N-(tert-butyl)6,7-dimethoxy-2-naphthaleneethylamine hydrochloride, m.p. 250°-251° C. (dec.).

EXAMPLE 45

A solution containing 27 g. of 6',7'-dimethoxy-2-(1-pyrrolidino)-2'-acetonaphthone hydrochloride in 300 ml. of 20% aqueous hydrochloric acid was shaken at 55° C. overnight under a hydrogen pressure of 20-50 psi in the presence of 300 mg. of 10% palladium-on-carbon. Two molar equivalents of hydrogen were absorbed. The catalyst was removed by filtration and the filtrate was evaporated to dryness in vacuo. Recrystallization of the residue from ethanol-ether afforded the hydrochloride as a hygroscopic solid. A 10.0-gram sample of the salt was partitioned between ether and dilute aqueous sodium hydroxide. The ethereal extracts were washed successively with water and saturated aqueous sodium chloride, dried over anhydrous sodium sulfate and evaporated to dryness in vacuo. The residue was recrystallized from aqueous methanol to give 5.0 g. of 1-[2-(6,7-dimethoxy-2-naphthyl)ethyl]-pyrrolidine, m.p. 94°-96° C.

EXAMPLE 46

A solution containing 112 g. of 2-(N,N-dibenzylamino)6',7'-dimethoxy-2'-acetonaphthone in 1.1 liters of dimethylformamide was shaken at 40°-50° C. under a hydrogen pressure of 20-50 psi in the presence of 10.0 g. of 10% palladium-on-carbon. After the absorption of three molar equivalents of hydrogen the catalyst was removed by filtration and the filtrate was evaporated to dryness in vacuo. The residue was dissolved in 1.2 liters of 2 N hydrochloric acid and hydrogenated overnight at 60°-65° C. in the presence of 10.0 g. of 10% palladium-on-carbon. The hydrogenation mixture was filtered warm and upon cooling the filtrate the product precipitated. Recrystallization from 95% ethanol afforded 39 g. of 6,7-dimethoxy-2-naphthaleneethylamine hydrochloride, m.p. 249°-250° C.

EXAMPLE 47

A solution containing 7.0 g. of 6-(2-chloroethyl)-2,3-dimethoxynaphthalene in 100 ml. of dimethylformamide was added dropwise to 100 ml. of stirred diethylamine at 0°-5° C. When the addition was complete the reaction mixture was allowed to come to room temperature and stirred overnight. After heating under reflux six hours the reaction mixture was evaporated to dryness in vacuo. The residue was partitioned between ether and water. The ethereal extracts were washed successively with water and saturated aqueous sodium chloride, dried over anhydrous magnesium sulfate and acidified with methanolic hydrogen chloride. The precipitated product was collected and the filtrate was evaporated to dryness in vacuo. The residue was again subjected to the above reaction conditions using 50 ml. of dimethylformamide and 50 ml. of diethylamine and a reflux period of two days. The products were combined and recrystallized from ethanol-ether to give 4.0 g. of N,N-diethyl-6,7-dimethoxy-2-naphthaleneethylamine hydrochloride, m.p. 195°–197° C.

EXAMPLE 48

To a suspension of 10.0 g. of N-methyl-6,7-dimethoxy-2-naphthaleneacetamide in 350 ml. of tetrahydrofuran at 0°–5° C. was added dropwise 140 ml. of a 1 M solution of borane in tetrahydrofuran. When the addition was complete the reaction mixture was stirred at 0°–5° C. for two hours, then at room temperature overnight and finally at the reflux temperature for six hours. The ice-cooled reaction mixture was then treated dropwise with 40 ml. of ethanol and the resulting solution acidified with ethanolic hydrogen chloride and kept cold two hours. The product was collected and recrystallized twice from methanol-ether to give 6.2 g. of 6,7-dimethoxy-N-methyl-2-naphthaleneethylamine hydrochloride, m.p. 230°–231° C.

EXAMPLE 49

Following a procedure similar to that in Example 48 but using 5.0 g. of N-ethyl-6,7-dimethoxy-2-naphthaleneacetamide and 60 ml. of 1 M solution of borane in tetrahydrofuran, there was obtained 3.5 g. of the hydrochloride which was partitioned between ether and aqueous diethylamine. Evaporation of the ether provided the free base which was redissolved in ether and acidified with methanolic hydrogen chloride to precipitate 2.6 g. of N-ethyl-6,7-dimethoxy-2-naphthaleneethylamine hydrochloride, m.p. 239°–241° C.

EXAMPLE 50

Following a procedure similar to that in Example 48 but using 8.0 g. of 1-(6,7-dimethoxy-2-naphthylacetyl)-piperidine and 120 ml. of a 1 M solution of borane in tetrahydrofuran, there was obtained 6.4 g. of 1-[2-(6,7-dimethoxy-2-naphthyl)ethyl]piperidine hydrochloride, m.p. 256°–247° C. (dec.).

EXAMPLE 51

Following a procedure similar to that in Example 48 but using 32.9 g. of 1-(6,7-dimethoxy-2-naphthylacetyl)-2-methylpiperidine and 300 ml. of a 1 M solution of borane in tetrahydrofuran, afforded 17.8 g. of 1-[2-(6,7-dimethoxy-2-naphthyl)ethyl]-2-methylpiperidine hydrochloride, m.p. 216°–227° C. (dec.).

EXAMPLE 52

Following a procedure similar to that in Example 48 but using 16.5 g. of 1-(6,7-dimethoxy-2-naphthylacetyl)-hexamethyleneimine and 150 ml. of a 1 M solution of borane in tetrahydrofuran afforded the hydrochloride which was warmed on the steam bath 2.5 hours in 15% aqueous sulfuric acid. The cooled solution was made alkaline with dilute potassium hydroxide. The precipitated free base was collected, dissolved in benzene, and the benzene-insoluble inorganic material was separated. The benzene was evaporated and the residue was recrystallized from aqueous methanol. The purified free base was then dissolved in ethanol and acidified with methanolic hydrogen chloride. The addition of ether precipitated 9.1 g. of 1-[(6,7-dimethoxy-2-naphthyl)ethyl]hexamethyleneimine hydrochloride, m.p. 255°–261° C. (dec.).

EXAMPLE 53

Following a procedure similar to that in Example 48 but using 9.0 g. of 4-(6,7-dimethoxy-2-naphthylacetyl)-morpholine and 120 ml. of a 1 M solution of borane in tetrahydofuran, there was obtained 7.5 g. of 4-[2-(6,7-dimethoxy-2-naphthyl)ethyl]morpholine hydrochloride, m.p. 237°–238° C. (dec.).

EXAMPLE 54

Following a procedure similar to that in Example 52 but using 9.0 g. of 6,7-dimethoxy-N-phenyl-2-naphthaleneacetamide and 110 ml. of a 1 M solution of borane in tetrahydrofuran afforded 2.9 g. of N-phenyl-6,7-dimethoxy-2-naphthaleneethylamine hydrochloride, m.p. 175°–177° C.

EXAMPLE 55

Following a procedure similar to that in Example 52 but using 14.0 g. of 6,7-dimethoxy-8-methyl-2-naphthaleneacetamide and 175 ml. of a 1 M solution of borane in tetrahydrofuran, yielded 13.0 g. of 6,7-dimethoxy-8-methyl-2-naphthaleneethylamine hydrochloride, m.p. 205°–215° C.

EXAMPLE 56

Following a procedure similar to that in Example 52 but using 10.0 g. of 6,7-diethoxy-2-naphthaleneacetamide and 115 ml. of a 1 M solution of borane in tetrahydrofuran, and isolating the product in the free-base form yielded 2.3 g. of 6,7-diethoxy-2-naphthalenethylamine, m.p. 109°–111° C. (benzene-n-hexane).

EXAMPLE 57

Following a procedure similar to that in Example 56 but using 10.0 g. of 1-(6,7-diethoxy-2-naphthylacetyl)-pyrrolidine and 97 ml. of a 1 M solution of borane in tetrahydrofuran afforded 7.0 g. of 1-[2-(6,7-diethoxy-2-naphthyl)ethyl]pyrrolidine, m.p. 71°–74° C.

EXAMPLE 58

A mixture of 13.0 g. of $\beta$-chloro-6,7-dimethoxy-$\alpha$-methyl-2-naphthaleneethylamine hydrochloride, 1.5 g. of 10% palladium-on-carbon and 200 ml. of dimethylformamide was shaken under a hydrogen pressure of 20–50 psi for six hours. The catalyst was removed by filtration and the filtrate was evaporated in vacuo. The residue was recrystallized from 2-propanol to give 8.8 g. of 6,7-dimethoxy-$\alpha$-methyl-2-naphthaleneethylamine hydrochloride, m.p. 226°–228° C.

EXAMPLE 59

To a stirred suspension of 0.5 g. of lithium aluminum hydride in 25 ml. of tetrahydrofuran at room temperature was added 1.0 g. of 6,7-dimethoxy-$\alpha,\alpha$-dimethyl-2-naphthaleneacetonitrile. The mixture was heated under reflux two hours, cooled and treated with 1 ml. of water and 3 ml. of 2 N aqueous sodium hydroxide, stirred one hour at room temperature then filtered. The filtrate was evaporated to dryness in vacuo and the residue was dissolved in ethyl acetate, washed with water, dried over anhydrous sodium sulfate and evaporated to dryness in vacuo. Recrystallization of the residue from aqueous methanol yielded 0.88 g. of 6,7-dimethoxy-$\beta,\beta$-dimethyl-2-naphthaleneethylamine, m.p. 66°–68° C. (resolidifies and melts at 105° C.).

This compound showed significant antihypertensive activity when administered orally at three dose levels of 12.5, 25 and 50 mg./kg. to adrenal regeneration hypertensive rats prepared according to the methods described by F. R. Shelton et al., Archives of Internal Medicine 98, 449 (1956) and Circulation Research Supplement 1, Vols. 24 and 25, May 1969 at pages I-35 through 56.

EXAMPLE 60

A solution containing 7.0 g. of 6,7-dimethoxy-1-naphthaleneacetonitrile in 200 ml. of 6.5 N methanolic ammonia was hydrogenated in the presence of Raney nickel under a hydrogen pressure of 40 psi at 40° C. for approximately eight hours. The catalyst was removed by filtration and the filtrate was evaporated in vacuo. The residue was dissolved in dilute hydrochloric acid, and the insoluble solids removed by filtration. The filtrate was made basic with dilute aqueous sodium hydroxide and extracted with ethyl acetate. Evaporation of the ethyl acetate afforded 6.3 g. of 6,7-dimethoxy-1-naphthaleneethylamine which was converted directly to 4.3 g. of 5-(2-aminoethyl)-2,3-naphthalenediol hydrochloride as described hereinabove in Example 13.

EXAMPLE 61

To a stirred mixture containing 2.0 g. of lithium aluminum hydride in 100 ml. of tetrahydrofuran was added portionwise 4.4 g. of 6,7-dimethoxy-1-naphthamide. The reaction mixture was stirred under reflux one hour, cooled and then treated successively with 2 ml. of water and 7 ml. of 2 N aqueous sodium hydroxide. The solids were removed by filtration and the filtrate evaporated to dryness in vacuo. The residue was recrystallized from benzene-n-hexane to give 3.4 g. of 6,7-dimethoxy-1-naphthalenemethylamine, m.p. 116°-118° C.

EXAMPLE 62

Following a procedure similar to that in Example 61 but using 14.0 g. of 6,7-dimethoxy-2-naphthamide and 4.0 g. of lithium aluminum hydride, there was obtained 11.0 g. of 6,7-dimethoxy-2-naphthalenemethylamine, m.p. 100°-104° C.

EXAMPLE 63

Following a procedure similar to that in Example 61 but using 31.1 g. of N-ethyl-6,7-dimethoxy-2-naphthamide and 4.6 g. of lithium aluminum hydride provided the amine which was dissolved in ethyl acetate, washed with water and saturated aqueous sodium chloride, dried over anhydrous magnesium sulfate and evaporated to dryness. The residue was dissolved in ethanol and acidified with methanolic hydrogen chloride. Addition of ether precipitated the salt. Two recrystallizations from 2-propanol afforded 9.8 g. of N-ethyl-6,7-dimethoxy-2-naphthalenemethylamine hydrochloride, m.p. 198°-206° C.

EXAMPLE 64

Following a procedure similar to that in Example 63 but using 33.0 g. N,N-diethyl-6,7-dimethoxy-2-naphthamide and 3.4 g. of lithium aluminum hydride, there was obtained 25.8 g. of N,N-diethyl-6,7-dimethoxy-2-naphthalenemethylamine hydrochloride, m.p. 201°-203° C.

EXAMPLE 65

Following a procedure similar to that in Example 63 but using 37.2 g. of 1-(6,7-dimethoxy-2-naphthoyl)pyrrolidine and 4.9 g. of lithium aluminum hydride yielded 15.7 g. of 1-[(6,7-dimethoxy-2-naphthyl)methyl]pyrrolidine hydrochloride, m.p. 225°-228° C.

EXAMPLE 66

A solution containing 20.0 g. of 2-bromo-6',7'-dimethoxy-2'-acetonaphthone in 350 ml. of acetonitrile was added over one hour to a stirred solution of 80 ml. of tert-butylamine in 500 ml. of acetontrile at −20° C. When the addition was complete the mixture was stirred an additional fifteen minutes at −20° C., then quenched in water and extracted with ether. The ethereal extracts were dried over anhydrous sodium sulfate and acidified with methanolic hydrogen chloride. The product was collected and recrystallized from methanol-ether to give 17.0 g. of 2-(tert-butylamino)-6',7'-dimethoxy-2'-acetonaphthone hydrochloride, m.p. >265° C. (dec.).

EXAMPLE 67

Following a procedure similar to that in Example 66 but using 20.0 g. of 2-bromo-6',7'-dimethoxy-1'-acetonaphthone and 80 ml. of tert-butylamine, there was obtained 8.5 g. of 2-(tert-butylamino)-6',7'-dimethoxy-1'-acetonaphthone hydrochloride, m.p. 230°-235° C.

EXAMPLE 68

Following a procedure similar to that in Example 66 but using 30.9 g. of 2-bromo-6',7'-dimethoxy-2'-acetonaphthone and 25 g. of benzylmethylamine there was obtained 38.5 g. of 2-(benzylmethylamino)-6',7'-dimethoxy-2'-acetonaphthone hydrochloride which was used immediately to prepare 6,7-dihydroxy-α-[(methylamino)methyl]-2-naphthalenemethanol as described in Example 26.

EXAMPLE 69

Following a procedure similar to that in Example 66 but using 23.0 g. of 2-bromo-6',7'-dimethoxy-2'-acetonaphthone and 29.5 g. of dibenzylamine afforded 26 g. of 2-(dibenzylamino)-6',7'-dimethoxy-2'-acetonaphthone hydrochloride, m.p. 185° C.

EXAMPLE 70

Following a procedure similar to that in Example 66 but using 20.0 g. of 2-bromo-6',7'-dimethoxy-2'-acetonaphthone and 60 ml. of 40% aqueous dimethylamine yielded 14.1 g. of 2-(dimethylamino)-6',7'-dimethoxy-2'-acetonaphthone hydrochloride, m.p. 236°-237° C. (dec.).

A 6.5-gram sample of this material, and 1.0 g. of 10% palladium-on-carbon in 100 ml. of dimethylformamide was shaken four hours under a hydrogen pressure of 30-50 psi. The catalyst was removed by filtration and the filtrate evaporated to dryness in vacuo. Recrystallization from methanol-ether yielded 5.4 g. of 6,7-dimethoxy-α-[(dimethylamino)methyl]-2-naphthalenemethanol hydrochloride, m.p. 219°-220° C. (dec.).

EXAMPLE 71

Following a procedure similar to that in Example 66 but using 50.0 g. of 2-bromo-6',7'-dimethoxy-2'-acetonaphthone and 50 ml. of pyrrolidine there was obtained 27 g. of 6',7'-dimethoxy-2-(1-pyrrolidino)-2'-acetonaphthone hydrochloride, m.p. 204°-206° C.

Catalytic reduction of a 7.8-gram sample of the above product according to a method similar to that in Example 70 provided 6.4 g. of 6,7-dimethoxy-α-[(1-pyrrolidinyl)methyl]-2-naphthalenemethanol hydrochloride, m.p. 224°-225° C. (dec.).

EXAMPLE 72

A solution containing 2.17 g. of diethyl acetamidomalonate in 25 ml. of dimethyl sulfoxide was added dropwise over fifteen minutes to a stirred mixture of 0.42 g. of a 57% mineral oil dispersion of sodium hydride in 20 ml. of dimethysulfoxide. After stirring twenty minutes at room temperature, a solution containing 2.36 g. of 6-(chloromethyl)-2,3-dimethoxynaphthalene in 20 ml. of dimethylsulfoxide was added dropwise over ten minutes. The resulting mixture was stirred overnight at room temperature then poured into water and extracted thoroughly with chloroform. The organic extracts were washed successively with water and saturated aqueous sodium chloride, dried over anhydrous sodium sulfate and evaporated to dryness. The residue was first triturated with n-hexane and finally recrystallized from benzene-ether-n-hexane to give 2.0 g. of diethyl 2-acetamido-2-(6,7-dimethoxy-2-naphthylmethyl)malonate, m.p. 130°–137° C.

EXAMPLE 73

A solution containing 4.39 g. of 6,8-dimethoxy-1-naphthaleneacetonitrile in 100 ml. of 5.6 N methanolic ammonia was shaken under a hydrogen pressure of 50 psi in the presence of Raney nickel until two molar equivalents of hydrogen were absorbed. The catalyst was removed by filtration and the filtrate was evaporated to dryness in vacuo. The residue was dissolved in toluene and the solution evaporated to dryness in vacuo and the process was repeated a second time. The residue was dissolved in a mixture of 10 ml. of ethanol and 50 ml. of toluene and treated with 3 ml. of 6 N ethanolic hydrogen chloride to give 4.15 g. of 6,8-dimethoxy-1-naphthaleneethylamine hydrochloride, m.p. 238° C. (dec.).

EXAMPLE 74

A solution containing 18.0 g. of 1,5-dimethoxy-4-(2-nitrovinyl)naphthalene in 150 ml. of tetrahydrofuran was added dropwise to a stirred suspension of 9.0 g. of lithium aluminum hydride in 100 ml. of tetrahydrofuran. When the addition was complete, the mixture was heated under reflux for six hours, then cooled and treated successively with 50 ml. of water, 10 ml. of 20% aqueous sodium hydroxide, 30 ml. of water and 170 ml. of dichloromethane. After stirring one hour the mixture was filtered and the filtrate evaporated in vacuo. The residue was dissolved in chloroform, dried over anhydrous sodium sulfate and evaporated to dryness. The residue was dissolved in methanol and acidified with methanolic hydrogen chloride. Evaporation to dryness left the crude salt which was partitioned between chloroform and dilute aqueous sodium hydroxide. The chloroform extracts were processed as above and the salt so obtained was repeatedly recrystallized from methanol-ether to give 7.3 g. of 4,8-dimethoxy-1-naphthaleneethylamine hydrochloride, m.p. 301°–305° C. (dec.).

EXAMPLE 75

A mixture containing 16.0 g. of α-[(dimethylamino)methyl]-4,8-dimethoxy-1-naphthalenemethanol hydrochloride, 2.0 g. of 10% palladium-on-carbon, 160 ml. of acetic acid, 20 ml. of water and 20 ml. of concentrated hydrochloric acid was shaken nine hours under a hydrogen pressure of 20–50 psi at room temperature. The catalyst was removed by filtration and the filtrate was evaporated to dryness in vacuo. The residue was dissolved in dilute aqueous hydrochloric acid, washed with ether and made alkaline with 10% aqueous potassium carbonate. The precipitated solid was collected, dissolved in chloroform, the solution dried over anhydrous magensium sulfate and evaporated to dryness. The residue was dissolved in ether and acidified with methanolic hydrogen chloride. Evaporation to dryness and recrystallization of the residue from absolute ethanol-ether afforded 8.5 g. of N,N-diethyl-4,8-dimethoxy-1-naphthaleneethylamine hydrochloride, m.p. 198°–199° C. (dec.).

EXAMPLE 76

Following a procedure similar to that described in Example 75 but using 18.0 g. of 4,8-dimethoxy-α-[(1-pyrrolidinyl)methyl]-1-naphthalenemethanol hydrochloride, there was obtained 12.4 g. of 1-[2-(4,8-dimethoxy-1-naphthyl)ethyl]pyrrolidine hydrochloride, m.p. 264°–265° C. (dec.).

EXAMPLE 77

A suspension of 13.3 g. of 2-(tert-butylamino)-4',8'-dimethoxy-1'-acetonaphthone in 800 ml. of tetrahydrofuran was added over 1.5 hours to a stirred suspension of 6.0 g. of lithium aluminum hydride in 200 ml. of tetrahydrofuran. When the addition was complete the reaction mixture was heated under reflux seventeen hours. The mixture was cooled, treated successively with 35 ml. of water, 25 ml. of 20% aqueous sodium hydroxide and 50 ml. of water, stirred one hour, diluted with 150 ml. of dichloromethane and filtered. The filtrate was evaporated to dryness in vacuo. The residue was triturated with ether and collected. The product was dissolved in methanol, acidified with methanolic hydrogen chloride and diluted with ether. The product was collected and recrystallized from methanol-ether to give 2.2 g. of α-[(tert-butylamino)methyl]-4,8-dimethoxy-1-naphthalenemethanol hydrochloride, m.p. 256°–257° C. (dec.).

EXAMPLE 78

Following a procedure similar to that described in Example 77 but using 22.0 g. of 2-(diethylamino)-4',8'-dimethoxy-1'-acetonaphthone and 8.0 g. of lithium aluminum hydride, there was obtained 18.3 g. of α-[(diethylamino)methyl]-4,8-dimethoxy-1-naphthalenemethanol hydrochloride, m.p. 183°–184° C. (dec.).

EXAMPLE 79

Following a procedure similar to that described in Example 77 but using 13.0 g. of 4',8'-dimethoxy-2-(1-pyrrolidinyl)-1'-acetonaphthone and 3.8 g. of lithium aluminum hydride yielded 6.7 g. of 4,8-dimethoxy-α-[(1-pyrrolidinyl)methyl]-1-naphthalenemethanol hydrochloride, m.p. 211°–212° C. (dec.).

EXAMPLE 80

A solution containing 26.5 g. of 2-chloro-4',8'-dimethoxy-1'-acetonaphthone in 150 ml. of acetonitrile was added dropwise to a stirred solution of 30 ml. of pyrrolidine in 200 ml. of acetonitrile. When the addition was complete the mixture was heated under reflux seventeen hours. The solvents were evaporated in vacuo and the residue was partitioned between dilute aqueous potassium carbonate and ether-ethyl acetate. The organic extracts were evaporated to dryness and the residue was dissolved in ether and extracted with dilute hydrochloric acid. The acidic extracts were made alkaline with 2 N aqueous sodium hydroxide and extracted with chloroform. The chloroform extracts were dried over anhydrous sodium sulfate and evaporated to dryness. The residue was dissolved in methanol, acidified with methanolic hydrogen chloride and diluted with ether. The product was collected and recrystallized twice from methanol-ether to give 24.0 g. of 4′,8′-dimethoxy-2-(1-pyrrolidinyl)-1′-acetonaphthone hydrochloride, m.p. 227°–228° C. (dec.).

EXAMPLE 81

Following a procedure similar to that described in Example 80 but using 30.0 g. 2-chloro-4′,8′-dimethoxy-1′-acetonaphthone and 150 ml. of diethylamine and isolating the product as the free base provided 25.5 g. of 2-(diethylamino)-4′,8′-dimethoxy-1′-acetonaphthone, m.p. 84°–85° C. (dec.).

A 2.5-gram sample of the base was converted to its salt as in Example 80 giving 2.1 g. of 2-(diethylamino)-4′,8′-dimethoxy-1′-acetonaphthone hydrochloride, m.p. 200°–202° C. (dec.).

EXAMPLE 82

Following a procedure similar to that described in Example 80 but using 100 ml. of tert-butylamine and 2-iodo-4′,8′-dimethoxy-1′-acetonaphthone obtained by reacting 24.7 g. of 2-chloro-4′,8′-dimethoxy-1′-acetonaphthone with 15.0 g. of sodium iodide in 400 ml. of refluxing acetone, there was obtained 17.0 g. of 2-(tert-butylamino)-4′,8′-dimethoxy-1′-acetonaphthone, m.p. 107°–110° C.

A 2.2-gram sample of the base was converted to its salt as in Example 80 giving 2.1 g. of 2-(tert-butylamino)-4′,8′-dimethoxy-1′-acetonaphthone hydrochloride, m.p. 233°–235° C. (dec.).

EXAMPLE 83

A mixture containing 17.9 g. of 6-methoxy-2-naphthaleneacetamide, 250 ml. of a 1 M solution of borane in tetrahydrofuran, and 350 ml. of tetrahydrofuran was heated under reflux for 36 hours. The mixture was cooled and treated dropwise with 30 ml. of methanol followed by 70 ml. of 4 N methanolic hydrogen chloride. The resulting mixture was stirred one hour at 0°–5° C., then ten hours at room temperature and finally one hour at the reflux temperature. Evaporation to dryness followed by recrystallization from methanol-ether afforded 11.5 g. of 6-methoxy-2-naphthaleneethylamine hydrochloride, m.p. 306°–308° C.

EXAMPLE 84

Following a procedure similar to that described in Example 83 but using 2.9 g. of N-ethyl-6-methoxy-2-naphthaleneacetamide and 36 ml. of a 1 M solution of borane in tetrahydrofuran, there was obtained 2.5 g. of N-ethyl-6-methoxy-2-naphthaleneethylamine hydrochloride, m.p. 247.5°–248° C.

EXAMPLE 85

A solution containing 5.8 g. of 1-(6-methoxy-2-naphthylacetyl)pyrrolidine in 125 ml. of tetrahydrofuran was added dropwise to a stirred, refluxing mixture of 1.7 g. of lithium aluminum hydride in 100 ml. of tetrahydrofuran. When addition was complete reflux was continued one hour. The cooled reaction mixture was treated successively with 8.5 ml. of water, 1.7 ml. of 20% aqueous sodium hydroxide, 5.5 ml. of water and 125 ml. of dichloromethane. The mixture was filtered and the filtrate evaporated to dryness. The residue was dissolved in chloroform, washed with water, dried over anhydrous potassium carbonate and evaporated to dryness. The residue was dissolved in ether and acidified with methanolic hydrogen chloride. The precipitated product was collected and recrystallized from methanol-ether to give 4.4 g. of 1-[2-(6-methoxy-2-naphthyl)ethyl]pyrrolidine hydrochloride, m.p. 230°–230.5° C.

EXAMPLE 86

Following a process similar to that described in Example 85 but using 4.0 g. of 1-[2-(6-methoxy-2-naphthyl)propionyl]pyrrolidine and 1.1 g. of lithium aluminum hydride, there was obtained 2.9 g. of 1-[2-(6-methoxy-2-naphthyl)propyl]pyrrolidine hydrochloride, m.p. 185.5°–186° C.

EXAMPLE 87

A mixture of 6.6 g. of 7-methoxy-2-naphthaleneacetonitrile, one teaspoon of Raney nickel, 7.5 ml. of liquid ammonia and 75 ml. of methanol was shaken under a hydrogen pressure of 1030 psi at room temperature 48 hours and then at 50° C. eight hours. The solvents were evaporated and the residue distilled under vacuum to give 4.2 g. of base (b.p. 105° C./0.05 mm.) which was dissolved in methanol, acidified with methanolic hydrogen chloride and diluted with ether to give 4.0 g. of 7-methoxy-2-naphthaleneethylamine hydrochloride, m.p. 265° C.

EXAMPLE 88

Following a procedure similar to that described in Example 83 but using 8.5 g. of 2-(6-methoxy-2-naphthyl)propionamide and 111 ml. of a 1 M solution of borane in tetrahydrofuran, there was obtained 6.7 g. of 6-methoxy-α-methyl-2-naphthaleneethylamine hydrochloride, m.p. 197°–198° C.

EXAMPLE 89

To a solution containing 10.8 g. of 6,7-dimethoxy-2-naphthaleneethylamine hydrochloride and 7.1 g. of benzylacetone in 260 ml. of warm methanol, adjusted to pH 6.0 with methanolic potassium hydroxide there was added 4.0 g. of 3A molecular sieve and a solution of 3.3 g. of sodium cyanoborohydride in 60 ml. of methanol. The reaction mixture was stirred at room temperature 72 hours while maintaining a pH of 5.5–6.5 by periodic addition of acetic acid. The reaction mixture was filtered, the filtrate acidified to pH 2 and evaporated. The residue was dissolved in 300 ml. of boiling methanol, filtered, the filtrate made strongly alkaline with 35% aqueous sodium hydroxide and decanted from the precipitated solids. The solids were washed with chloroform and the washings were combined with the methanol supernatant and filtered. The filtrate was evaporated to dryness. The residue was dissolved in ether and acidified with 6 N methanolic hydrogen chloride. The product was collected and recrystallized from methanol-ether to give 5.7 g. of N-(1-methyl-3-phenylpropyl)-6,7-dimethoxy-2-naphthaleneethylamine hydrochloride, m.p. 188°–190° C.

EXAMPLE 90

Following a procedure similar to that described in Example 89 but using 5.4 g. of 6,7-dimethoxy-2-naphthaleneethylamine hydrochloride, 4.0 g. of p-methoxybenzylacetone and 1.7 g. of sodium cyanoborohydride, there was obtained 3.7 g. of N-[3-(p-methoxyphenyl)-1-methylpropyl]-6,7-dimethoxy-2-naphthaleneethylamine hydrochloride, m.p. 190°–191° C.

EXAMPLE 91

To a stirred suspension of 13.2 g. of α-(1-aminoethyl)-6,7-dimethoxy-2-naphthalenemethanol in 125 ml. of chloroform was added dropwise 10 ml. of thionyl chloride. When the addition was complete the mixture was heated under reflux one hour, and then evaporated to dryness in vacuo. The residue was dissolved in 100 ml. of acetone and dry hydrogen chloride was passed into the solution to precipitate the product. There was obtained 12.2 g. of β-chloro-6,7-dimethoxy-α-methyl-2-naphthaleneethylamine hydrochloride, m.p. 190°–192° C. (dec.).

EXAMPLE 92

A solution containing 40.0 g. of crude 6,7-dimethoxy-2-naphthaleneacetyl chloride in 500 ml. of ether was added over 0.5 hours to one liter of stirred 20% aqueous methylamine at 0° C. The resulting mixture was allowed to stand until the ether had evaporated. The product was collected and recrystallized from aqueous methanol to give 17.5 g. of N-methyl-6,7-dimethoxy-2-naphthaleneacetamide, m.p. 167°–169° C.

EXAMPLE 93

Following a procedure similar to that described in Example 92 but using 44 g. of 6,7-dimethoxy-2-naphthaleneacetyl chloride in 500 ml. of an ether-tetrahydrofuran mixture and one liter of 20% aqueous ethylamine, afforded 26.0 g. of N-ethyl-6,7-dimethoxy-2-naphthaleneacetamide, m.p. 152°–154° C.

EXAMPLE 94

Following a procedure similar to that described in Example 92 but using 12.0 g. of 6,7-dimethoxy-2-naphthaleneacetyl chloride and 20.0 g. of piperidine, there was obtained 8.3 g. of 1-(6,7-dimethoxy-2-naphthylacetyl)piperidine, m.p. 85°–87° C.

EXAMPLE 95

Following a procedure similar to that described in Example 92 but using 12.0 g. of 6,7-dimethoxy-2-naphthaleneacetyl chloride and 20.0 g. of morpholine yielded 9.3 g. of 4-(6,7-dimethoxy-2-naphthylacetyl)morpholine, m.p. 137°–139° C.

EXAMPLE 96

Following a procedure similar to that described in Example 92 but using 40 g. of 6,7-dimethoxy-2-naphthaleneacetyl chloride and 1 liter of 20% aqueous diethylamine, there was obtained 38 g. of N,N-diethyl-6,7-dimethoxy-2-naphthaleneacetamide, m.p. 69°–71° C.

EXAMPLE 97

To a stirred solution containing the crude acid chloride obtained from 60.0 g. of 6,7-dimethoxy-2-naphthaleneacetic acid in ether, there was added dropwise 60 ml. of pyrrolidine. After standing overnight the reaction mixture was partitioned between ethyl acetate and water; the organic layer was washed successively with dilute hydrochloric acid, water, and saturated aqueous sodium chloride, dried over sodium sulfate, and evaporated to dryness in vacuo. Recrystallization of the residue from benzene-n-hexane afforded 54.0 g. of 1-(6,7-dimethoxy-2-naphthylacetyl)pyrrolidine, m.p. 100°–101° C.

EXAMPLE 98

To the crude acid chloride prepared from 24.0 g. 6,7-dimethoxy-8-methyl-2-naphthaleneacetic acid was added with swirling 450 ml. of cold concentrated aqueous ammonia. After standing at room temperature three hours, the product was collected and recrystallized from ethyl acetate to give 15.0 g. of 6,7-dimethoxy-8-methyl-2-naphthaleneacetamide, m.p. 180°–183° C.

EXAMPLE 99

To 300 ml. of stirred concentrated aqueous ammonia was added 15.0 g. of 6,7-diethoxy-2-naphthaleneacetyl chloride. The mixture was stirred five hours. The solid product was dissolved in ethyl acetate, washed successively with water, dilute hydrochloric acid, aqueous sodium bicarbonate, and saturated aqueous sodium chloride, dried over anhydrous sodium sulfate and evaporated to dryness. Recrystallization of the residue from methanol afforded 11.0 g. of 6,7-diethoxy-2-naphthaleneacetamide, m.p. 154°–156° C.

EXAMPLE 100

Following a procedure similar to that described in Example 99 but using 15.0 g. of 6,7-diethoxy-2-naphthaleneacetyl chloride and 40 ml. of pyrrolidine, there was obtained 11.0 g. of 1-(6,7-diethoxy-2-naphthylacetyl)pyrrolidine, m.p. 93°–95° C.

EXAMPLE 101

A solution containing 19.0 g. of aniline in 150 ml. of benzene was added dropwise to a stirred solution of 15.0 g. of 6,7-dimethoxy-2-naphthaleneacetyl chloride in 300 ml. of benzene. When the reaction was complete the mixture was washed with 10% hydrochloric acid, 10% aqueous sodium hydroxide, water, and finally saturated aqueous sodium chloride, dried over anhydrous magnesium sulfate and evaporated to dryness. The residue was recrystallized from chloroform-n-hexane to give 9.5 g. of 6,7-dimethoxy-N-phenyl-2-naphthaleneacetamide, m.p. 140°–141° C.

EXAMPLE 102

Following a procedure similar to that described in Example 99 but using 525 ml. of 35% aqueous hexamethyleneimine and 30 g. of 6,7-dimethoxy-2-naphthaleneacetyl chloride, there was obtained 17.1 g. of 1-(6,7-dimethoxy-2-naphthylacetyl)-hexamethyleneimine, m.p. 51°–62° C.

EXAMPLE 103

To a solution containing 3.6 ml. of 2-methylpiperidine in 300 ml. of tetrahydrofuran was added dropwise a solution of the crude acid chloride, obtained from 25.0 g. of 6,7-dimethoxy-2-naphthaleneacetic acid, in 500 ml. of tetrahydrofuran. The mixture was stirred two hours at room temperature and then evaporated to dryness in vacuo. The residue was dissolved in ether, washed successively with water, 2 N hydrochloric acid, saturated aqueous sodium bicarbonate and water, dried over anhydrous magnesium sulfate and evaporated leaving 33.9 g. of 1-(6,7-dimethoxy-2-naphthylacetyl)-2-methylpiperidine which was subsequently converted to 1-[2-(6,7-dimethoxy-2-naphthyl)ethyl]-2-methylpiperidine hydrochloride as described hereinabove in Example 51.

EXAMPLE 104

A solution containing 62.4 g. of bromine in 500 ml. of chloroform was added dropwise to a stirred solution of 90.0 g. of 6',7'-dimethoxy-2'-acetonaphthone at room temperature. When the addition was complete the chloroform solution was washed successively with water, saturated aqueous sodium bicarbonate and water, dried over anhydrous magnesium sulfate and evaporated to dryness in vacuo. Trituration with n-hexane afforded 73.0 g. of 2-bromo-6',7'-dimethoxy-2'-acetonaphthone, m.p. 135°–136° C.

EXAMPLE 105

Following a procedure similar to that described in Example 104 but using 2.3 g. of 6',7'-dimethoxy-1'-acetonaphthone and 1.6 g. of bromine, there was obtained 2.2 g. of 2-bromo-6',7'-dimethoxy-1'-acetonaphthone, m.p. 115°–117° C.

EXAMPLE 106

To a stirred solution of 50.0 g. of p-toluenesulfonyl chloride in 350 ml. of pyridine at 0° C. there was added 26.0 g. of 2-(6,7-dimethoxy-2-naphthyl)ethanol. The mixture was stirred seven hours at room temperature, and then poured over ice. The product was extracted with ethyl acetate, washed successively with water, dilute hydrochloric acid and saturated aqueous sodium chloride, dried over anhydrous sodium sulfate and evaporated to dryness. The residue was triturated with ether and filtered to give 14.0 g. of 2-(6,7-dimethoxy-2-naphthyl)ethyl p-toluenesulfonate, m.p. 103°–104° C. The filtrate was evaporated to dryness and the residue crystallized from methanol giving 7.0 g. of 6-(2-chloroethyl)-2,3-dimethoxynaphthalene which was converted directly to N,N-diethyl-6,7-dimethoxy-2-naphthaleneethylamine hydrochloride as described hereinabove in Example 47.

EXAMPLE 107

A solution containing 2.27 g. of 6,7-dimethoxy-2-naphthaleneacetonitrile and 2 ml. of methyl iodide in 25 ml. of dimethylformamide was added over ten minutes to a mixture of 1.0 g. of a 57% mineral oil dispersion of sodium hydride in 25 ml. of dimethylformamide. When the addition was complete the mixture was stirred two hours at room temperature and then 0.5 hours on the steam bath. After cooling, the reaction mixture was quenched in water and the product collected and recrystallized from aqueous methanol to give 2.2 g. of 6,7-dimethoxy-$\alpha,\alpha$-dimethyl-2-naphthaleneacetonitrile, m.p. 126°–127° C.

EXAMPLE 108

To a stirred mixture of 12.0 g. of powdered sodium cyanide in 140 ml. of dimethyl sulfoxide was added portionwise over 10 minutes 20.0 g. of 5-chloromethyl-2,3-dimethoxynaphthalene. When the addition was complete stirring was continued for an additional 0.5 hours. The reaction was poured into a large volume of water and extracted with ethyl acetate. The organic extracts were washed with water and saturated aqueous sodium chloride, dried over anhydrous sodium sulfate and evaporated to dryness. The residue was recrystallized from benzene-n-hexane to give 18.0 g. of 6,7-dimethoxy-1-naphthaleneacetonitrile, m.p. 128°–130° C.

EXAMPLE 109

Following a procedure similar to that described in Example 108 but using 19.0 g. of 6-chloromethyl-2,3-dimethoxynaphthalene and 10.0 g. of sodium cyanide there was obtained 7.5 g. of 6,7-dimethoxy-2-naphthaleneacetonitrile, m.p. 88°–90° C.

EXAMPLE 110

To 500 ml. of stirred 25% aqueous pyrrolidine at 0° C. was added 35.0 g. of 6,7-dimethoxy-2-naphthoyl chloride. The mixture was stirred at 0° C. ten minutes then at room temperature three hours. The product was collected and washed with water to give 39.4 g. of 1-(6,7-dimethoxy-2-naphthoyl)pyrrolidine, m.p. 123°–126° C.

EXAMPLE 111

Following a procedure similar to that described in Example 110 but using 35.0 g. of 6,7-dimethoxy-2-naphthoyl chloride and 500 ml. of 35% aqueous diethylamine provided 34.7 g. of N,N-diethyl-6,7-dimethoxy-2-naphthamide, m.p. 108°–110° C.

EXAMPLE 112

Following a procedure similar to that described in Example 110 but using 34.0 g. of 6,7-dimethoxy-2-naphthoyl chloride and 500 ml. of 35% aqueous ethylamine, there was obtained 32.5 g. of N-ethyl-6,7-dimethoxy-2-naphthamide, m.p. 164°–166° C.

EXAMPLE 113

Following a procedure similar to that described in Example 98 but using the crude acid chloride obtained from 15.0 g. of 6,7-dimethoxy-2-naphthoic acid, and 300 ml. of concentrated aqueous ammonia, there was obtained 15.0 g. of 6,7-dimethoxy-2-naphthamide, m.p. 183°–188° C.

EXAMPLE 114

Following a procedure similar to that described in Example 98 but using the crude acid chloride obtained from 0.5 g. of 6,7-dimethoxy-1-naphthoic acid, and 30 ml. of concentrated aqueous ammonia there was obtained 0.39 g. of 6,7-dimethoxy-1-naphthamide, m.p. 187°–189° C.

EXAMPLE 115

A solution containing 29.1 g. of 6,8-dimethoxy-1,2,3,4-tetrahydro-1-naphthylideneacetonitrile and 22.8 g. of N-bromosuccinimide in 350 ml. of carbon tetrachloride was heated at reflux three hours under a tungsten-filament flood lamp. The cooled reaction mixture was filtered and the filtrate was washed successively with saturated aqueous sodium bicarbonate, 10% aqueous sodium bisulfite and water, dried over anhydrous sodium sulfate and evaporated to dryness. Repeated recrystallization of the residue from carbon tetrachloride yielded 3.0 g. of 6,8-dimethoxy-1-naphthaleneacetonitrile, m.p. 106°–109° C.

EXAMPLE 116

A mixture containing 22.0 g. of 4,8-dimethoxy-1-naphthaldehyde, 30 ml. of nitromethane, 15.0 g. of ammonium acetate and 200 ml. of acetic acid was heated under reflux six hours. The reaction mixture was evaporated to dryness in vacuo and the residue was partitioned between dilute aqueous sodium bicarbonate and ether. The ethereal solution was washed with 10% aqueous potassium carbonate and dried over anhydrous magnesium sulfate. Evaporation of the ether yielded 17.9 g. of 1,5-dimethoxy-4-(2-nitrovinyl)naphthalene which was converted directly to 7.3 g. of 4,8-dimethoxy-1-naphthaleneethylamine hydrochloride as described hereinabove in Example 74.

EXAMPLE 117

To a stirred mixture of 18.0 g. of 1,5-dimethoxynaphthalene and 13.3 g. of aluminum chloride in 300 ml. of dichloromethane at room temperature was added dropwise a solution containing 11.4 g. of α-chloroacetyl chloride in 50 ml. of dichloromethane. When the addition was complete, stirring at room temperature was continued 48 hours. The mixture was diluted with chloroform, washed with dilute hydrochloric acid, dried over anhydrous sodium sulfate, and evaporated to dryness. The residue was extracted with ether-n-hexane. Evaporation of the extracts and recrystallization of the residue from ether-n-hexane afforded 14.2 g. of 2-chloro-4',8'-dimethoxy-1'-acetonaphthone, m.p. 80°–82° C.

EXAMPLE 118

Following a procedure similar to that described in Example 92 but using the crude acid chloride obtained from 4.3 g. of 6-methoxy-2-naphthaleneacetic acid, and 60 ml. of 20% aqueous ammonia, there was obtained 2.4 g. of 6-methoxy-2-naphthaleneacetamide, m.p. 238°–239° C.

EXAMPLE 119

A solution containing 33 ml. of ethylamine in 330 ml. of ether was added over 0.5 hours to a stirred solution of 22.0 g. of 6-methoxy-2-naphthaleneacetyl chloride in 900 ml. of ether at 0°–5° C., and stored overnight at 4° C. The precipitated solid was collected and extracted with chloroform. The extracts were washed with water, dried over anhydrous potassium carbonate and evaporated to dryness to give 19.0 g. of N-ethyl-6-methoxy-2-naphthaleneacetamide, m.p. 156°–157° C.

EXAMPLE 120

Following a procedure similar to that described in Example 119 but using 5.6 g. of 6-methoxy-2-naphthaleneacetyl chloride and 3.6 g. of pyrrolidine, there was obtained 6.0 g. of 1-(6-methoxy-2-naphthylacetyl)-pyrrolidine, m.p. 104.5°–105° C.

EXAMPLE 121

Following a procedure similar to that described in Example 119 but using 11.0 g. of 2-(6-methoxy-2-naphthyl)-propionyl chloride and 7.6 g. of pyrrolidine, there was obtained 12.4 g. of 1-[2-(6-methoxy-2-naphthyl)propionyl]-pyrrolidine, which was converted directly to 1-[2-(6-methoxy-2-naphthyl)propyl]pyrrolidine hydrochloride as described hereinabove in Example 86.

EXAMPLE 122

Following a procedure similar to that described in Example 92 but using 11.0 g. of 2-(6-methoxy-2-naphthyl)-propionyl chloride and 265 ml. of 20% aqueous ammonia, yielded 9.0 g. of 2-(6-methoxy-2-naphthyl)-propionamide, m.p. 160° C.

EXAMPLE 123

A solution containing 29.7 g. of 3,4-dihydro-7-methoxy-2-naphthaleneacetonitrile in 300 ml. of xylene was heated under reflux 24 hours in the presence of 3.0 g. of 10% palladium-on-carbon. The catalyst was removed by filtration and the filtrate was evaporated to dryness in vacuo. Trituration of the residue with chloroform-hexane afforded 5.2 g. of 7-methoxy-2-naphthaleneacetonitrile, m.p. 84° C.

EXAMPLE 124

A solution containing 18.1 g. of 2-dibenzylamino-6'-methoxy-2'-propionaphthone in 200 ml. of dimethylformamide was shaken at 50° C. overnight in the presence of 2.0 g. of 10% palladium-on-carbon under a hydrogen pressure of 40–50 psi. The catalyst was removed by filtration and the filtrate was evaporated to dryness in vacuo. The residue was dissolved in methanol-ether and acidified with methanolic hydrogen chloride. The product was collected and recrystallized twice from methanol-ether to give 6.2 g. of 6-methoxy-α-(1-aminoethyl)-2-naphthalenemethanol hydrochloride, m.p. 247°–248.5° C.

EXAMPLE 125

A mixture containing 41.0 g. of 2-bromo-6'-methoxy-2'-propionaphthone and 55.2 g. of dibenzylamine in 400 ml. of acetonitrile was stirred at room temperature 24 hours. The precipitated solid was collected and extracted with chloroform. The chloroform-insoluble material was separated and the filtrate was evaporated to dryness. The residue was triturated with cold ether-n-hexane to give 31.0 g. of 2-(dibenzylamino)-6-methoxy-2'-propionaphthone, m.p. 130°–132° C.

EXAMPLE 126

A mixture of 20.5 g. of 2-hydroxyimino-6',7'-dimethoxy-2'-propionaphthone, 2 g. of 30% palladium-on-carbon, 31 ml. of concentrated hydrochloric acid and sufficient ethanol to give a total volume of 200 ml. was shaken under a hydrogen pressure of 50 psi at 65° C. approximately five hours. The mixture was diluted with water, the catalyst was removed by filtration, and the filtrate was concentrated. The precipitated product was dissolved in dilute hydrochloric acid and washed with ether. The aqueous portion was made alkaline with 35% aqueous sodium hydroxide. The precipitate was dissolved in chloroform, washed with water and saturated aqueous sodium chloride, dried over anhydrous magnesium sulfate and evaporated to dryness to give 17.0 g. of α-(1-aminoethyl)-6,7-dimethoxy-2-naphthalenemethanol, m.p. 165°–172° C.

EXAMPLE 127

To a stirred solution containing 50.0 g. of 6,7-dimethoxy-2-naphthaleneacetic acid at 0°–5° C. was added dropwise 40 ml. of thionyl chloride. After the addition was complete the reaction mixture was warmed to room temperature and then at 40° C. two hours. The reaction mixture was evaporated to dryness in vacuo and the residue recrystallized from ether-n-hexane to give 28 g. of 6,7-dimethoxy-2-naphthaleneacetyl chloride, m.p. 56°–62° C.

EXAMPLE 128

A mixture of 24.0 g. of 6,7-dimethoxy-8-methyl-2-naphthaleneacetic acid and 30 ml. of thionyl chloride in 250 ml. of benzene was kept at 40° C. one hour and then overnight at room temperature. The reaction mixture was then evaporated to dryness in vacuo at 50° C. Additional benzene was added and evaporation repeated to give 6,7-dimethoxy-8-methyl-2-naphthaleneacetyl chloride. An infrared spectrum indicated no remaining carboxylic acid and this material was used directly in the preparation of 6,7-dimethoxy-8-methyl-2-naphthaleneacetamide as described hereinabove in Example 98.

EXAMPLE 129

Following a procedure similar to that described in Example 128 but using 27 g. of 6,7-diethoxy-2-naphthaleneacetic acid, 20 ml. of thionyl chloride and one drop of dimethylformamide, there was obtained 31.0 g. of 6,7-diethoxy-2-naphthaleneacetyl chloride which was used directly in the preparation of 6,7-diethoxy-2-naphthaleneacetamide and 1-(6,7-diethoxy-2-naphthylacetyl) pyrrolidine as described hereinabove in Examples 99 and 100, respectively.

EXAMPLE 130

A solution containing 49.2 g. of 6,7-dimethoxy-2-naphthaleneacetic acid in 200 ml. of tetrahydrofuran was added to a stirred solution of 7.6 g. of lithium aluminum hydride in 200 ml. of tetrahydrofuran. When the addition was complete the mixture was heated under reflux one hour, then cooled and treated with 8 ml. of water followed by 20 ml. of 2 N aqueous sodium hydroxide, and stirred two hours at room temperature. The mixture was then filtered and the solvent allowed to evaporate over two days. The remaining solid was dissolved in ethyl acetate, washed successively with dilute aqueous sodium hydroxide, water, and saturated aqueous sodium chloride, dried over anhydrous magnesium sulfate and evaporated to dryness. Recrystallization of the residue from benzene-n-hexane afforded 29.0 g. of 2-(6,7-dimethoxy-2-naphthyl)ethanol, m.p. 122°–124° C.

EXAMPLE 131

A mixture of 26.0 g. of 6,7-dimethoxy-1-naphthalenemethanol, 60.0 g. of anhydrous sodium sulfate and 2 liters of benzene was stirred at room temperature two hours while hydrogen chloride was bubbled in over two hours. The mixture was filtered and the filtrate evaporated to dryness. The residue was recrystallized from cyclohexane to give 20.0 g. of 5-chloromethyl-2,3-dimethoxynaphthalene, m.p. 99°–102° C.

EXAMPLE 132

Following a procedure similar to that described in Example 131 but using 29.0 g. of 6,7-dimethoxy-2-naphthalenemethanol and 40 g. of anhydrous sodium sulfate there was obtained 24.0 g. of 6-chloromethyl-2,3-dimethoxynaphthalene, m.p. 96°–110° C.

EXAMPLE 133

To a solution containing 15.0 g. of 6,7-dimethoxy-2-naphthoic acid and one drop of dimethylformamide in 200 ml. of benzene was added 25 ml. of thionyl chloride. After heating one hour under reflux the mixture was evaporated to dryness in vacuo. Additional benzene was added and evaporation repeated to give 6,7-dimethoxy-2-naphthoyl chloride which was used directly in the preparation of 6,7-dimethoxy-2-naphthamide as described hereinabove in Example 113.

EXAMPLE 134

Following a procedure similar to that described in Example 133 but using 0.5 g. of 6,7-dimethoxy-1-naphthoic acid and 1 ml. of thionyl chloride, there was obtained 6,7-dimethoxy-1-naphthoyl chloride which was used directly in the preparation of 6,7-dimethoxy-1-naphthamide as described hereinabove in Example 114.

EXAMPLE 135

To a stirred mixture of 13.9 g. of a 57% mineral oil dispersion of sodium hydride in 400 ml. of glyme (freshly distilled from lithium aluminum hydride) was added dropwise 53 ml. of diethyl phosphonoacetonitrile. After 15 minutes a solution containing 60.0 g. of 6,8-dimethoxy-1-tetralone in 100 ml. of glyme was added dropwise. After stirring overnight at room temperature the mixture was poured into 3 liters of ice-water, stirred 0.5 hours and filtered. The product was recrystallized from absolute ethanol to give 54.0 g. of 1,2,3,4-tetrahydro-6,8-dimethoxy-1-naphthylideneacetonitrile, m.p. 101°–102° C.

EXAMPLE 136

Following a procedure similar to that described in Example 108 but substituting for 5-chloromethyl-2,3-dimethoxynaphthalene an equivalent amount of 7-chloromethyl-1,3-dimethoxynaphthalene there is obtained 6,8-dimethoxy-2-naphthaleneacetonitrile.

EXAMPLE 137

Following a procedure similar to that described in Example 131 but substituting for 6,7-dimethoxy-1-naphthalenemethanol an equivalent amount of 6,8-dimethoxy-2-naphthalenemethanol there is obtained 7-chloromethyl-1,3-dimethoxynaphthalene.

EXAMPLE 138

To a stirred mixture of 7.1 g. of a 57% mineral oil dispersion of sodium hydride in 400 ml. of dry glyme under nitrogen was added dropwise 28.0 g. of diethyl phosphonoacetonitrile followed by a solution of 25.5 g. of 7-methoxy-2-tetralone in 50 ml. of glyme. After stirring four hours at room temperature the mixture was allowed to stand overnight under nitrogen. The mixture was decanted from an insoluble residue; the supernatant was concentrated in vacuo, and poured into 350 ml. of ice-water. The product was extracted with chloroform and the extracts were washed with water, dried over anhydrous magnesium sulfate and evaporated to dryness to give 29.9 g. of 3,4-dihydro-7-methoxy-2-naphthaleneacetonitrile which was converted directly to 7-methoxy-2-naphthaleneacetonitrile as described hereinabove in Example 123.

EXAMPLE 139

A suspension of 15.0 g. of 2-hydroxyimino-6',7'-dimethoxy-2'-propionaphthone in 500 ml. of absolute ethanol was treated with 25 ml. of 3 N aqueous sodium hydroxide. To the resulting clear solution was added 4.2 g. of sodium borohydride. After stirring 2.5 hours at room temperature the mixture was acidified and filtered. The filtrate was made basic with saturated aqueous sodium bicarbonate and evaporated to dryness in vacuo. The residue was extracted with boiling ethyl acetate and isopropyl acetate. The organic extracts were concentrated and cooled to give 7.2 g. of 1-(6,7-dimethoxy-2-naphthyl)-1-hydroxy-2-propanone oxime, m.p.

185°–186° C. Concentration of the mother liquors afforded an additional 3.5 g., m.p. 178°–181° C.

EXAMPLE 140

Hydrogen chloride was bubbled into a refluxing solution containing 23.4 g. of 6',7'-dimethoxy-2'-propionaphthone in 200 ml. of benzene and 650 ml. of ether while 15 ml. of amyl nitrite was added dropwise to the mixture. After standing overnight at room temperature the mixture was heated to reflux while an additional 5 ml. of amyl nitrite was added over two hours. The mixture was poured on ice and the organic layer was washed with water and then thoroughly extracted with 10% aqueous sodium hydroxide. Acidification of the alkaline extracts with 6 N hydrochloric acid preparation 23.2 g. of 2-hydroxyimino-6',7'-dimethoxy-2'-propionaphthone, m.p. 185°–188° C.

EXAMPLE 141

A mixture of 383 g. of 4-(6,7-dimethoxy-2-naphthylthioacetyl)morpholine, 250 g. of sodium hydroxide and 800 ml. of water was heated under reflux six hours. The mixture was evaporated in vacuo and the residue dissolved in 4 liters of warm water. The aqueous solution was treated with concentrated hydrochloric acid until a red impurity separated. The still-basic solution was cooled and filtered and the filtrate was acidified with concentrated hydrochloric acid to give 210 g. of 6,7-dimethoxy-2-naphthaleneacetic acid, m.p. 140°–143° C.

EXAMPLE 142

A mixture of 4-(6,7-dimethoxy-8-methyl-2-naphthylthioacetyl)morpholine obtained from 41 g. of 6',7'-dimethoxy-8'-methyl-2'-acetonaphthone, 80 ml. of ethanol and 200 ml. of 35% aqueous sodium hydroxide was heated under reflux one hour. The cooled reaction mixture was diluted with 200 ml. of water and washed with chloroform. The aqueous solution was acidified with dilute hydrochloric acid and the precipitated acid was dissolved in chloroform, washed with water and saturated aqueous sodium chloride, dried over anhydrous magnesium sulfate and evaporated to dryness. The residue was recrystallized from benzene-n-hexane to give 25.0 g. of 6,7-dimethoxy-8-methyl-2-naphthaleneacetic acid, m.p. 115°–120° C.

EXAMPLE 143

A stirred solution containing 35.0 g. of 6,7-dihydroxy-2-naphthaleneacetic acid and 50 g. of solid potassium hydroxide in 350 ml. of water was heated to 85° C. and treated portionwise with 70 ml. of diethyl sulfate. Another 25 g. of potassium hydroxide was added followed by 40 ml. of diethyl sulfate. This was repeated twice more. The solution was then cooled, filtered and acidified with hydrochloric acid. The precipitated product was dissolved in chloroform, washed with water, dried over anhydrous magnesium sulfate and evaporated to dryness. The residue was recrystallized from diisopropyl ether to give 27.0 g. of 6,7-diethoxy-2-naphthaleneacetic acid, m.p. 117°–120° C.

EXAMPLE 144

To a refluxing solution containing 129.0 g. of 6,7-dimethoxy-2-naphthaleneacetic acid in 1 liter of acetic acid, there is added dropwise, at a rate to maintain a clear solution, 2 liters of 48% hydrobromic acid. When the addition was complete reflux was maintained for an additional 40 minutes. Cooling the mixture in ice afforded 101.5 g. of 6,7-dihydroxy-2-naphthaleneacetic acid, m.p. 218°–222° C.

EXAMPLE 145

Following a procedure similar to that described in Example 130 but using 46.4 g. of 6,7-dimethoxy-2-naphthoic acid and 7.6 g. of lithium aluminum hydride there was obtained 29 g. of 6,7-dimethoxy-2-naphthalenemethanol, m.p. 110°–112° C.

EXAMPLE 146

Following a procedure similar to that described in Example 130 but using 1.23 g. of 6,7-dimethoxy-1-naphthoic acid and 0.20 g. of lithium aluminum hydride, there was obtained 0.58 g. of 6,7-dimethoxy-1-naphthalenemethanol, m.p. 128°–129° C.

EXAMPLE 147

Following a procedure similar to that described in Example 155 but substituting for 1,2,3,4-tetrahydro-6,8-dimethoxy-1-oxo-2-naphthaldehyde ethylene acetal an equivalent amount of 6,8-dimethoxy-2-naphthaldehyde, there is obtained 6,8-dimethoxy-2-naphthalenemethanol.

EXAMPLE 148

A stirred mixture of 10.3 g. of 6',7'-dimethoxy-2'-acetonaphthone, 2.4 g. of sulfur and 6.5 g. of morpholine was slowly heated to 155° C. and maintained at this temperature ten hours. Trituration with ethanol produced 12.0 g. of 4-(6,7-dimethoxy-2-naphthylthioacetyl)morpholine, m.p. 155°–165° C. Recrystallization from benzene raised the melting point to 173°–175° C.

EXAMPLE 149

A stirred mixture of 2.0 g. of 6',7'-dimethoxy-8'-methyl-2'-acetonaphthone, 0.48 g. of sulfur and 1.3 g. of morpholine was heated two hours at 140° C. The mixture was cooled and the residue recrystallized from methanol to give 4-(6,7-dimethoxy-8-methyl-2-naphthylthioacetyl)morpholine, m.p. 100°–103° C.

EXAMPLE 150

To a stirred solution containing 1 liter of 5.25% aqueous sodium hypochlorite (Chlorox®) and 80 ml. of 35% aqueous sodium hydroxide at 50° C. was added 30 g. of 6',7'-dimethoxy-1'-acetonaphthone. The mixture was heated at 70°–80° C. for five hours. Five 100 ml. portions of hypochlorite were added periodically to maintain a positive starch-iodide test. When all of the solid had dissolved the reaction mixture was cooled, and treated with saturated aqueous sodium bisulfite until a negative starch-iodide test was obtained. The mixture was filtered and the filtrate was acidified with concentrated hydrochloric acid to precipitate 26.0 g. of 6,7-dimethoxy-1-naphthoic acid, m.p. 230°–234° C.

EXAMPLE 151

A refluxing solution containing 218 mg. of 3,4-dihydro-6,8-dimethoxy-2-naphthaldehyde and 196 mg. of N-bromosuccinimide in 10 ml. of carbon tetrachloride was irradiated three hours with a tungsten-filament flood lamp. After irradiation was stopped, reflux was continued an additional two hours. The cooled mixture was filtered, washed with saturated aqueous sodium bicarbonate, dried over anhydrous sodium sulfate and evaporated to dryness. The residue was recrystallized from ethanol to give 50 mg. of 6,8-dimethoxy-2-naphthaldehyde, m.p. 165° C.

EXAMPLE 152

To a stirred solution containing 55.0 g. of 2,3-dimethoxy-1-methylnaphthalene and 23.0 g. of acetyl chloride in 650 ml. of sym-tetrachloroethane at 0° C. was added portionwise 41.0 g. of aluminum chloride. When the addition was complete the mixture was stirred three hours at room temperature, diluted with chloroform, and poured into cold dilute hydrochloric acid. The organic layer was washed with water, dried over anhydrous sodium sulfate and evaporated to dryness. Recrystallization of the residue from benzene-n-hexane afforded 42.0 g. of 6',7'-dimethoxy-8'-methyl-2'-acetonaphthone, m.p. 103°–106° C.

EXAMPLE 153

To a stirred solution containing 960 g. of 2,3-dimethoxynaphthalene and 430 ml. of acetyl chloride in 6.0 liters of sym-tetrachloroethane at 0° C. was added portionwise 800 g. of aluminum chloride. The mixture was stirred 3.5 hours at room temperature and then poured into 10 liters of ice-water and 500 ml. of concentrated hydrochloric acid. The layers were separated and the aqueous portion extracted with chloroform. The combined organic extracts were dried over anhydrous potassium carbonate, concentrated and diluted with 3 liters of methanol. Cooling and filtering afforded 952 g. of 6',7'-dimethoxy-2'-acetonaphthone. The mother liquors were concentrated and diluted with methanol to give 37.0 g. of product which after recrystallization from methanol afforded 26.5 g. of 6',7'-dimethoxy-1'-acetonaphthone, m.p. 141°–143° C. Recrystallization of the major product from methanol gave 918 g. of 6',7'-dimethoxy-2'-acetonaphthone, m.p. 110°–112° C.

EXAMPLE 154

To a solution containing 4.0 g. of 1,2,3,4-tetrahydro-1-hydroxy-6,8-dimethoxy-2-naphthaldehyde ethylene acetal in 40 ml. of acetic acid was added a solution of 4 ml. of concentrated sulfuric acid in 36 ml. of water. The mixture was stirred two hours at room temperature and then poured into 200 ml. of water and extracted with ether. The ethereal extracts were washed successively with water, saturated aqueous sodium bicarbonate and saturated aqueous sodium chloride, dried over anhydrous sodium sulfate and evaporated to dryness. The residue was recrystallized from absolute ethanol to give 750 mg. of 3,4-dihydro-6,8-dimethoxy-2-naphthaldehyde, m.p. 100°–102° C.

EXAMPLE 155

A mixture of crude 1,2,3,4-tetrahydro-6,8-dimethoxy-1-oxo-2-naphthaldehyde ethylene acetal obtained from 5.73 g. of 2-hydroxymethylene-6,8-dimethoxy-1-tetralone, and 0.91 g. of sodium borohydride in 25 ml. of 2-propanol was stirred two hours at room temperature. The mixture was cooled and treated with 80 ml. of saturated aqueous ammonium chloride and extracted with ether. The ethereal extracts were washed with saturated aqueous solutions of sodium bicarbonate and sodium chloride, dried over anhydrous magnesium sulfate and evaporated to dryness to give 1,2,3,4-tetrahydro-1-hydroxy-6,8-dimethoxy-2-naphthaldehyde ethylene acetal which was converted directly to 3,4-dihydro-6,8-dimethoxy-2-naphthaldehyde as described hereinabove in Example 154.

EXAMPLE 156

A solution containing 5.73 g. of 2-hydroxymethylene-6,8-dimethoxy-1-tetralone, 2.23 g. of ethylene glycol and 100 mg. of p-toluenesulfonic acid in 25 ml. of benzene was heated at reflux two hours under a Dean-Stark water separator. The mixture was filtered, the filtrate was washed with saturated aqueous solutions of sodium bicarbonate and sodium chloride, dried over anhydrous magnesium sulfate and evaporated to dryness in vacuo to give 1,2,3,4-tetrahydro-6,8-dimethoxy-1-oxo-2-naphthaldehyde ethylene acetal which was converted directly to 1,2,3,4-tetrahydro-1-hydroxy-6,8-dimethoxy-2-naphthaldehyde ethylene acetal as described hereinabove in Example 155.

We claim:
1. A compound having, in the free base form, the formula

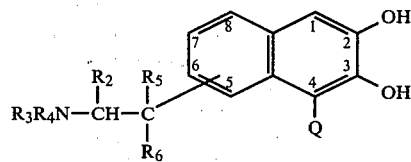

wherein the side chain represented by

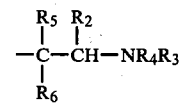

occupies either position 5 or position 6 of the naphthalene nucleus;

$Q$ is hydrogen or methyl;

$R_5$ and $R_6$ are independently hydrogen or methyl;

$R_2$ is hydrogen or methyl, provided that when $R_5$ and/or $R_6$ are methyl, then $R_2$ is hydrogen;

$R_3$ and $R_4$ are independently hydrogen, lower-alkyl, benzyl, or aryl;

or an acid-addition salt thereof.

2. A compound according to claim 1 wherein $Q$ is hydrogen.

3. A compound according to claim 2 wherein $R_5$ and $R_6$ are hydrogen.

4. A compound according to claim 3 wherein $R_2$ is hydrogen.

5. A compound according to claim 4 wherein the side chain represented by -$CH_2$-$CH_2$-$NR_4R_3$ occupies position 6 of the naphthalene nucleus.

6. A compound according to claim 5 wherein $R_3$ and $R_4$ are hydrogen.

7. 6-(2-Aminoethyl)-2,3-naphthalenediol hydrochloride according to claim 6.

8. 6-(2-Aminopropyl)-2,3-naphthalenediol hydrochloride according to claim 3.

9. 5-(2-Aminoethyl)-2,3-naphthalenediol hydrochloride according to claim 4.

10. 6-(2-Aminoethyl)-4-methyl-2,3-naphthalenediol hydrochloride according to claim 1.

11. 6-[2-(Ethylamino)ethyl]-2,3-naphthalenediol hydrochloride according to claim 5.

12. 6-[2-(Dimethylamino)ethyl]-2,3-naphthalenediol hydrochloride according to claim 5.

13. 6-[2-(Methylamino)ethyl]-2,3-naphthalenediol hydrochloride according to claim 5.

14. 6-[2-(Diethylamino)ethyl]-2,3-naphthalenediol hydrochloride according to claim 5.

15. 6-(2-Anilinoethyl)-2,3-naphthalenediol hydrochloride according to claim 5.

16. A compound according to claim 2 wherein $R_5$ and $R_6$ are methyl and $R_2$ is hydrogen.

17. A compound according to claim 16 wherein the side chain represented by

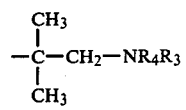

occupies position 6 of the naphthalene nucleus.

18. A compound according to claim 16 wherein $R_3$ and $R_4$ are independently hydrogen or lower-alkyl.

19. A compound according to claim 18 wherein $R_3$ and $R_4$ are hydrogen.

20. 6-(2-Amino-1,1-dimethylethyl)-2,3-naphthalenediol hydrochloride according to claim 19.

* * * * *